United States Patent [19]
Winters et al.

[11] Patent Number: 6,033,111
[45] Date of Patent: Mar. 7, 2000

[54] COLOR CODING METHOD AND APPARATUS FOR AN X-RAY POSITIONING SYSTEM

[75] Inventors: William Winters, New Rochelle; Howard Wolf, Port Washington, both of N.Y.

[73] Assignee: Wolf X-Ray Corporation, West Hempstead, N.Y.

[21] Appl. No.: 09/196,020

[22] Filed: Nov. 20, 1998

[51] Int. Cl.[7] .................................................. A61B 6/14

[52] U.S. Cl. ............................ 378/170; 378/168; 378/205

[58] Field of Search ..................................... 378/170, 168, 378/205

[56] References Cited

U.S. PATENT DOCUMENTS

| | | |
|---|---|---|
| 3,962,807 | 6/1976 | Pantone . |
| 4,048,506 | 9/1977 | Updegrave .............................. 250/479 |
| 5,289,919 | 3/1994 | Fischer . |

*Primary Examiner*—David P. Porta
*Assistant Examiner*—Michael J. Schwartz
*Attorney, Agent, or Firm*—Frommer Lawrence & Haug LLP; I. Marc Asperas

[57] ABSTRACT

Color coding the components of a dental positioner, including an aiming ring, a bite block and an indicator arm allows the operator to assemble the correct positioner for proper positioning and alignment according to a particular dental area to be X-rayed. The color coding corresponds to different dental areas including the anterior and posterior dental areas. For coronal areas, a bite-wing block is provided which also may be in the color coded.

26 Claims, 24 Drawing Sheets

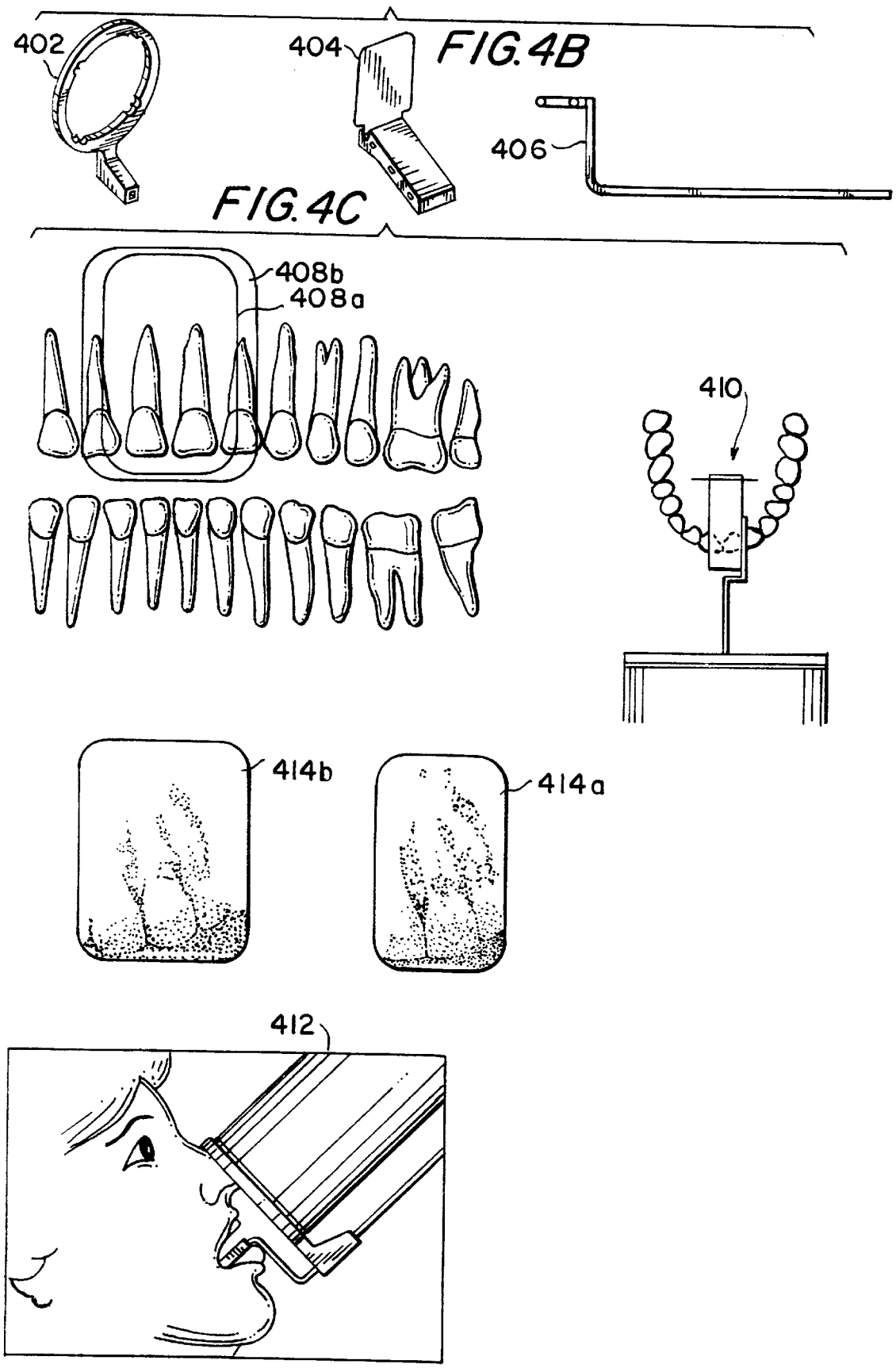

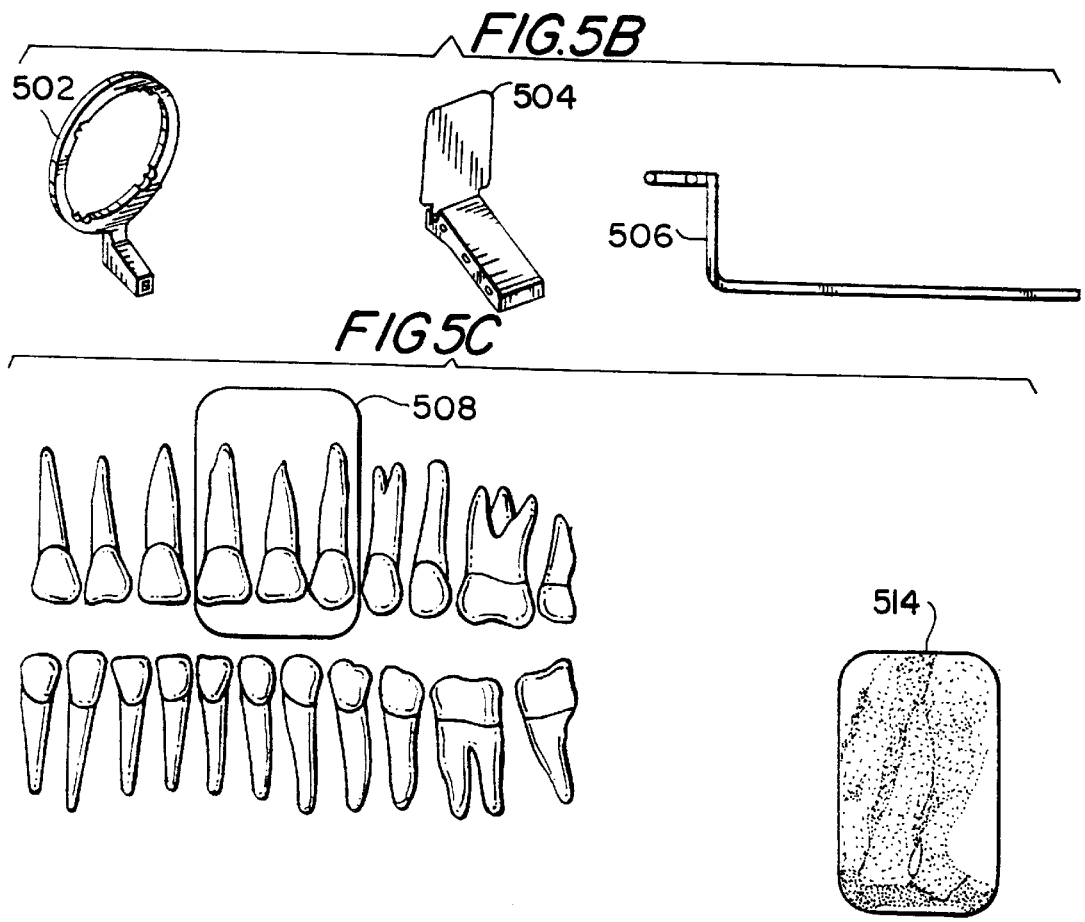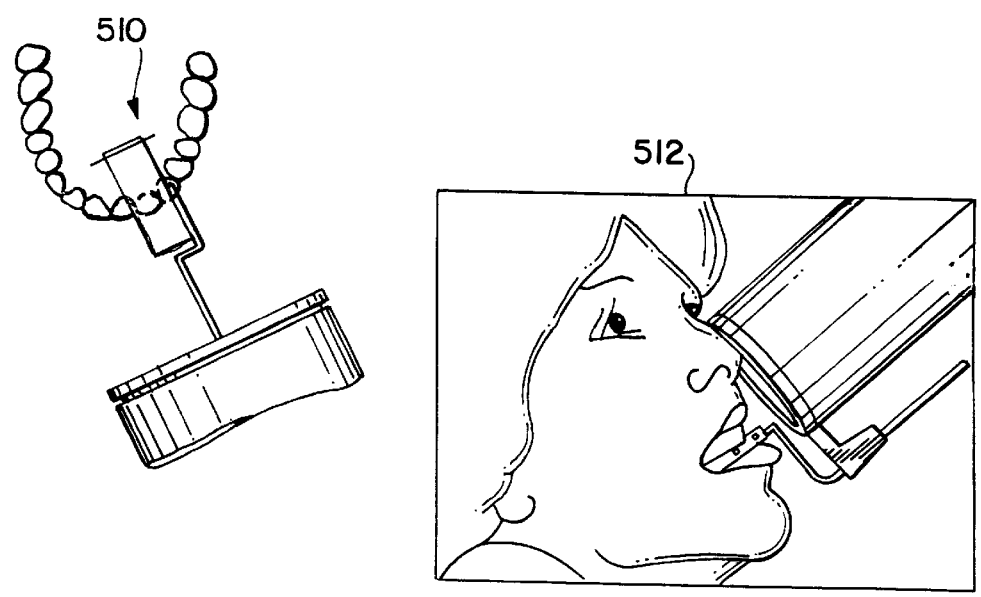

600A — ASSEMBLE THE ANTERIOR INSTRUMENT USING THE ANTERIOR LOCALIZING RING AND THE ANTERIOR INDICATOR ARM ALONG WITH AN ANTERIOR BITE-BLOCK. INSERT THE FILM, VERTICALLY, INTO THE BITE-BLOCK, MAKING SURE THE ALL-WHITE SIDE OF THE FILM IS FACING THE X-RAY PID. USUALLY A SIZE 1 (ANTERIOR SIZE) FILM IS REQUIRED. SHOULD YOU USE #2 FILM (ADULT SIZE PERIAPICAL) YOU MAY WISH OT CURL THE ANTERIOR CORNER SLIGHTLY TO AID IN POSITIONING THE INSTRUMENT

↓

600B — POSITION THE FILM ON THE CUSPID AND FIRST BICUSPID CENTERED ONTO THE FILM. USE THE ENTIRE HORIZONTAL LENGTH OF THE BITE-BLOCK TO POSITION THE FILM WELL INTO THE POSTERIOR ASPECT.

↓

600C — WITH THE BITE-BLOCK PORTION OF THE FILM POSITIONER (THE HORIZONTAL PART) PLACED ON THE MAXILLARY EDGE OF THE TEETH TO BE RADIOGRAPHED, INSTRUCT THE PATIENT TO BITE DOWN FIRMLY IN ORDER TO HOLD THE FILM IN PROPER POSITION.
(AS AN OPTION YOU MAY INCLUDE A COTTON ROLL OR "CUSHIE" BETWEEN THE FILM POSITIONER AND THE INCISAL EDGE FOR ADDED PATIENT COMFORT.)

↓

600D — SLIDE THE LOCALIZING RING ALONG THE INDICATOR ARM UNTIL IT IS CLOSE TO THE SKIN.

↓

600E — ALIGN THE PID OF THE X-RAY UNIT TO THE LOCALIZING RING, MAKING SURE THE PID IS CENTERED TO THE LOCALIZING RING.

↓

600F — EXPOSE THE FILM, FOLLOWING THE X-RAY MACHINE AND/OR FILM MANUFACTURER'S IMPULSE RECOMMENDATIONS.

↓

600G — ASK THE PATIENT TO OPEN THEIR MOUTH, AND GENTLY REMOVE THE ENTIRE POSITIONING DEVICE. REMOVE THE FILM FOR PROCESSING.

*FIG. 6A*

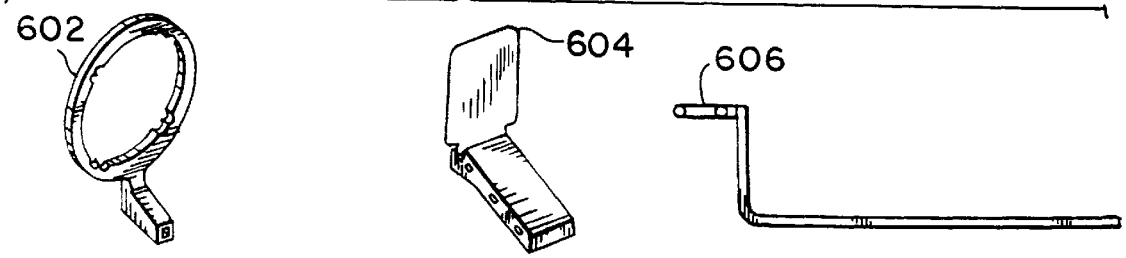
FIG.6B
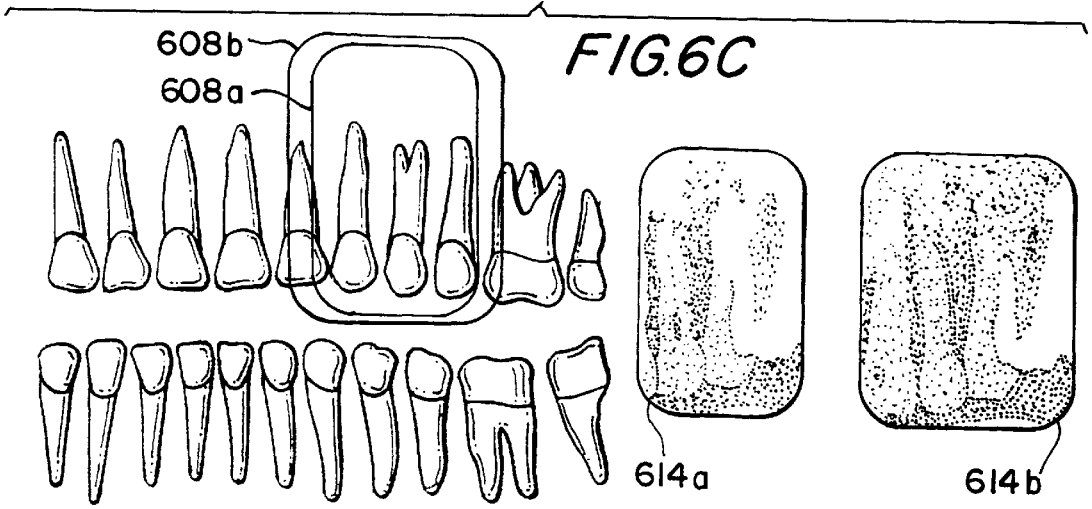
FIG.6C
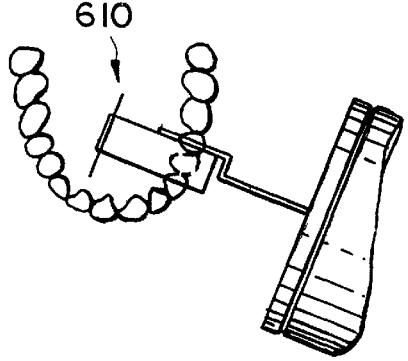
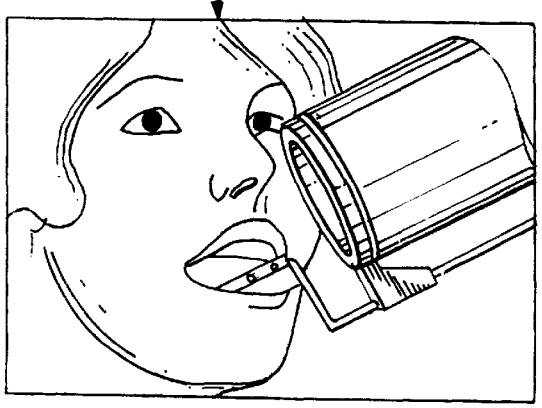

```
700A ── ASSEMBLE THE POSTERIOR INSTRUMENT USING THE
        POSTERIOR LOCALIZING RING AND THE POSTERIOR
        INDICATOR ARM ALONG WITH A POSTERIOR BITE-BLOCK.
        INSERT THE FILM, VERTICALLY, INTO THE BITE-BLOCK,
        MAKING SURE THE ALL-WHITE SIDE OF THE FILM IS FACING
        THE X-RAY PID. YOU MAY WISH TO CURL THE UPPER
        ANTERIOR CORNER SLIGHTLY TO AID IN POSITIONING THE
        INSTRUMENT.
                              ↓
700B ── CENTER THE FILM ON THE SECOND BICUSPID. USE THE
        ENTIRE HORIZONTAL LENGTH OF THE BITE-BLOCK TO
        POSITION THE FILM WELL IN THE MID-PALATAL ASPECT.
                              ↓
700C ── WITH THE BITE-BLOCK PORTION OF THE FILM POSITIONER
        (THE HORIZONTAL PART) PLACED ON THE OCCLUSAL
        SURFACE OF THE TEETH TO BE RADIOGRAPHED, INSTRUCT
        THE PATIENT TO BITE DOWN FIRMLY IN ORDER TO HOLD
        THE FILM IN PROPER POSITION.
        (AS AN OPTION YOU MAY INCLUDE A COTTON ROLL OR
        "CUSHIE" BETWEEN THE FILM POSITIONER AND THE INCISAL
        EDGE FOR ADDED PATIENT COMFORT.)
                              ↓
700D ── SLIDE THE LOCALIZING RING ALONG THE INDICATOR ARM
        UNTIL IT IS CLOSE TO THE SKIN.
                              ↓
700E ── ALIGN THE PID OF THE X-RAY UNIT TO THE LOCALIZING
        RING, MAKING SURE THE PID IS CENTERED TO THE
        LOCALIZING RING.
                              ↓
700F ── EXPOSE THE FILM, FOLLOWING THE X-RAY MACHINE
        AND/OR FILM MANUFACTURER'S IMPULSE
        RECOMMENDATIONS.
                              ↓
700G ── ASK THE PATIENT TO OPEN THEIR MOUTH, AND GENTLY
        REMOVE THE ENTIRE POSITIONING DEVICE. REMOVE THE
        FILM FOR PROCESSING.
```

*FIG. 7A*

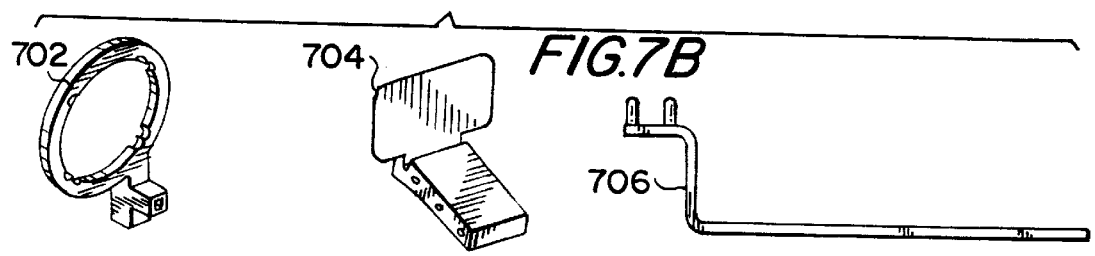
FIG. 7B
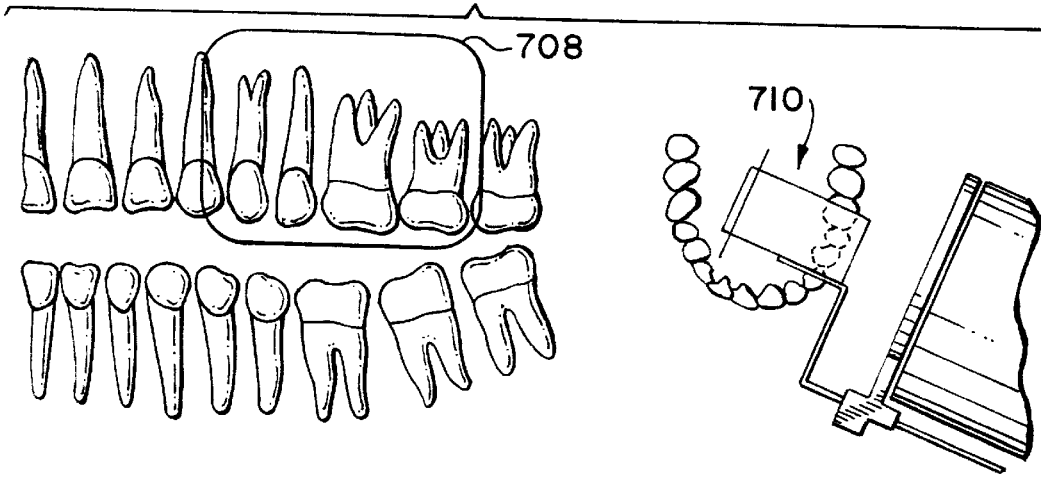
FIG. 7C
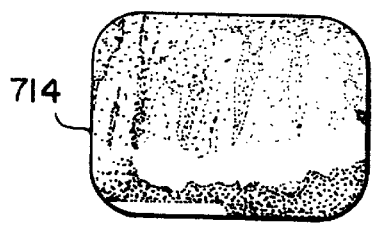
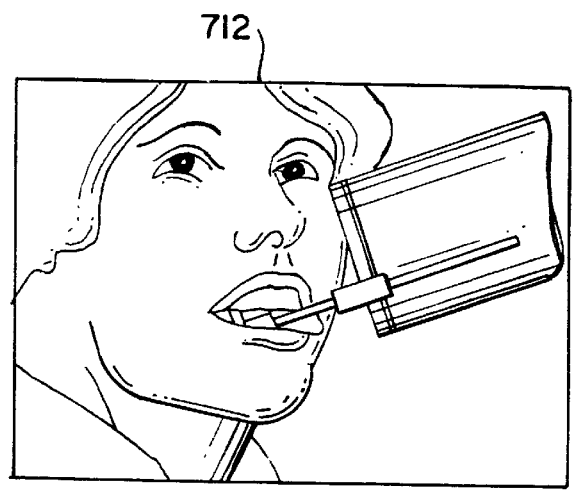

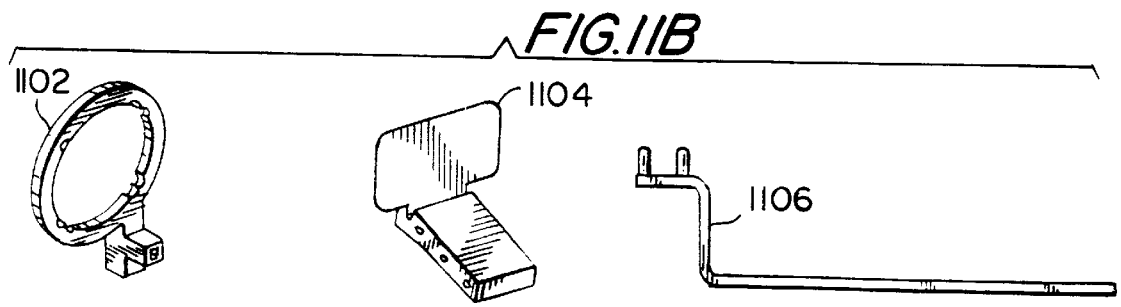
FIG.11B
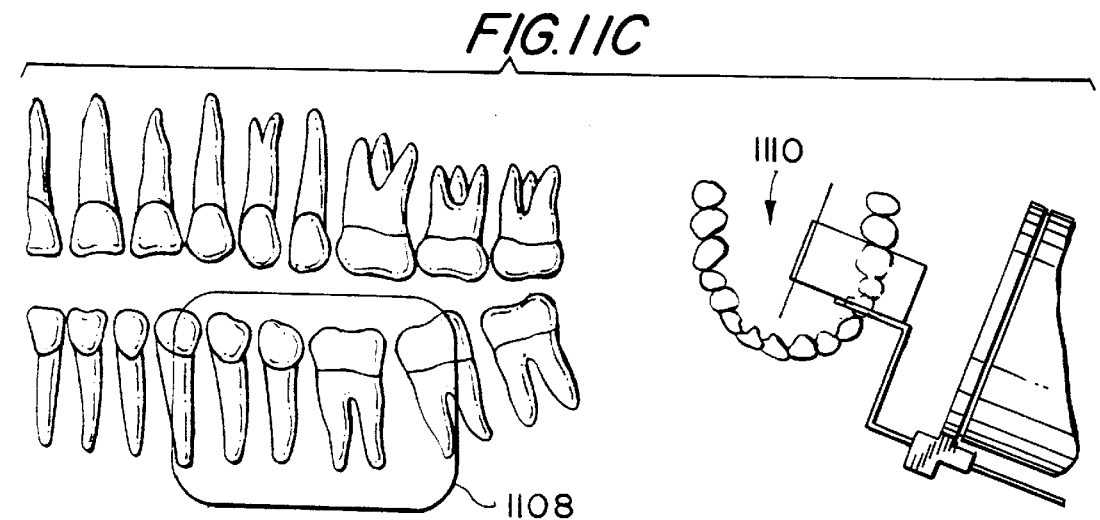
FIG.11C
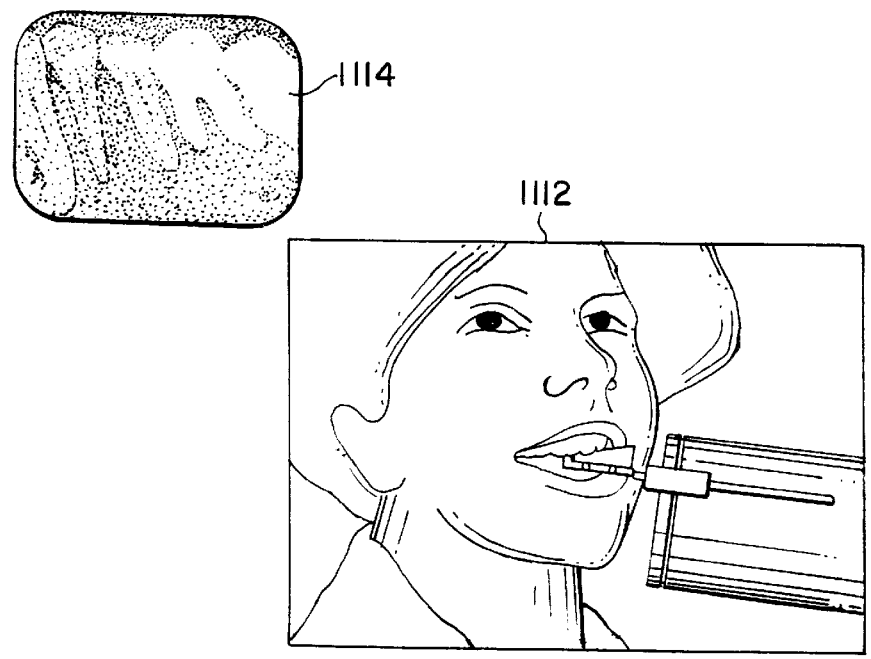

COLOR CODING METHOD AND APPARATUS FOR AN X-RAY POSITIONING SYSTEM

BACKGROUND OF THE INVENTION

1. Field of the Invention

The present invention relates to a color coding method and apparatus and, more particularly, a color coding method and apparatus for an X-ray positioning system.

2. Description of the Related Art

The dental X-ray is vital to the diagnosis and treatment of the patient's teeth. The dental X-ray provides the dentist with a quick and accurate picture of the patient's teeth with which the dentist initially diagnoses a new patient's teeth and determines the course of treatment which may include root canals, cavity feelings, wisdom teeth extractions, etc. Since the dental X-ray provides the dentist with an interior picture of the teeth, the dentist can determine almost immediately what the condition of the teeth is and what course of action to take in the treatment of the teeth. The dental X-ray is so fundamental to the dentist's practice that it is the first thing the dentist requires when treating a new patient.

Dental X-raying techniques have evolved over the years. The most primitive dental X-ray technique involved the dentist placing a small X-ray film within the patient's mouth and exposing the X-ray film to X-rays from an X-ray machine emitter which was placed proximate to the patient's face such that the X-ray is directed to the X-ray film.

It was determined that the best quality X-ray images were obtained by the so-called "paralleling technique" whose basic principle for intraoral periapical films is that the film and the long axis of the tooth being radial graphed is parallel to each other, and the central ray of the X-ray beam is directed perpendicular to both. To accomplish this parallelism, it was determined that the object, i.e. tooth, to film distance must be increased.

Problematically, this object-to-film distance was sizeable in some areas, such as the maxillary molar position where the X-ray film was held in the midline of the palate of the mouth, to achieve this parallelism. This made holding the X-ray film in the patient's mouth difficult while the X-ray film was exposed. Another problem is that the increased object-to-film distance resulted in a loss of image definition, or sharpness.

In order to compensate for this loss of definition due to the sizeable object-to-film distance, it was found that a 16 inch focal film distance was necessary. To implement the 16 inch focal film distance, a long cone was attached to the X-ray emitter which functioned to provide this distance. Unfortunately, the "long cone technique" as it has become to be known, emphasizes the length of the PID rather than the parallel relationship of the object and the film.

In order to assist the dentist in positioning the film parallel to the teeth with such a long cone, positioners were developed which couple the cone to the film such that the cone and film are in alignment. As shown in FIG. 1, for example, the positioner comprises an aiming ring 100 which attaches to the cone 102, an indicator arm 104 which is held by the aiming ring and a bite-block 106 which holds the X-ray film. With this arrangement, the dentist need only position the film parallel to the teeth and the film, teeth and cone are in alignment such that the film and the teeth are parallel and the cone of the X-ray beam is perpendicular to both.

However, positioners do not take into account the different areas of the patient's mouth, known as the four quadrants. Problematically, each of the four quadrants of the patient's mouth requires different types of X-ray films, has different bites and is in different positions of the patient's mouth. Thus, there are different X-ray films for X-raying different teeth, different bite-blocks to receive different bites from the patient's mouth and different indicator arms for positioning the X-ray film in the proper position in the areas of the patient's mouth. In addition, the aiming ring needed to be modified for different positions in order to properly direct the indicator arm to the desired area of the patient's mouth.

This led to the dental practice of interchanging the X-ray films, the bite-blocks, the indicator arms and the aiming rings to achieve parallelism when X-raying different teeth in the patient's mouth. Problematically, the many interchangeable X-ray films, bite-blocks, indicator arms and aiming rings were confusing which resulted in the dentist needlessly wasting time determining the correct "set-up" for the desired teeth to be X-rayed. In practice, the dentist found that the proper combination of interchangeable parts could be found only through trial and error leading to further wasted time and discomfort of the patient. In addition, dental assistants likewise found the interchangeable parts confusing and often required the assistance of the dentist which detracted the dentist from other duties such as attending to other patients in the dental office. Since the patient's bill is based on the amount of time the dentist and dental technicians spend with the patient, the unnecessarily wasted time determining the correct combination of interchangeable parts for performing the dental X-ray was reflected in the patients bill.

Heretofore, there has been no system by which the dentist or dental technician quickly and easily determines the correct combination of X-ray film, bite-block, indicator arm and aiming ring for a particular dental area to be X-rayed.

OBJECTS AND SUMMARY OF THE INVENTION

It is an object of the present invention to provide a quick and easy method and apparatus for determining the correct combination of components for performing a dental X-ray on a particular dental area.

The present invention provides a color coding method and apparatus for an X-ray positioning system. In one particular aspect thereof, one or more components of the positioning system including a positioning or aiming ring, an indicator arm and bite-block or bite-wing block such that the dentist or dental assistant quickly identifies the correct components for assembling a particular positioner for X-raying a particular dental area.

BRIEF DESCRIPTION OF THE DRAWINGS

FIGS. 4A–4C illustrate the method for X-raying the maxillary incisor region;

FIGS. 5A–5C illustrate the method for X-raying the maxillary lateral incisor region;

FIGS. 6A–6C illustrate the method for X-raying the maxillary cuspid region;

FIGS. 7A–7C illustrate the method for X-raying the maxillar bicuspid (premolar) region;

FIGS. 11A–11C illustrate the method for X-raying the mandibular bicuspid (premolar) region;

DETAILED DESCRIPTION OF THE PREFERRED EMBODIMENT

Figure 1:
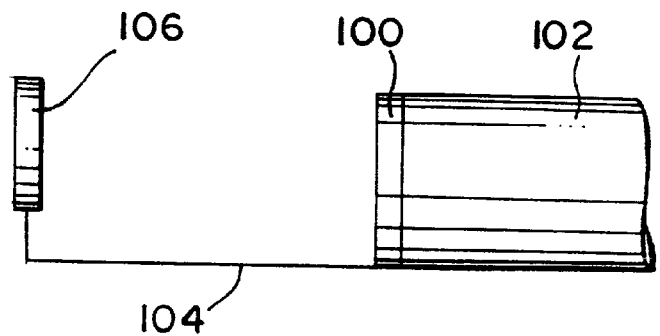
FIG. 1 illustrates the conventional positioner.
Figure 2A:
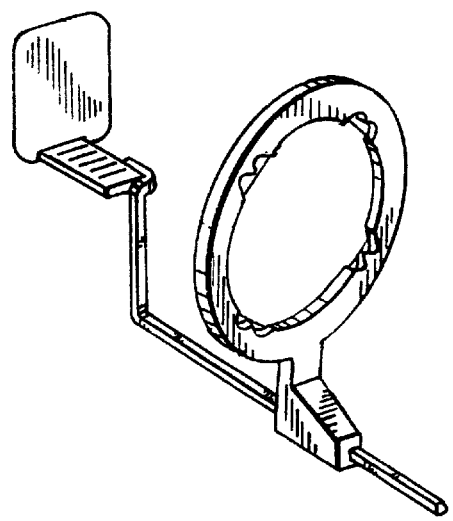
FIGS. 2A and 2B illustrate the color coding method and apparatus of the present invention.
Figure 2B:
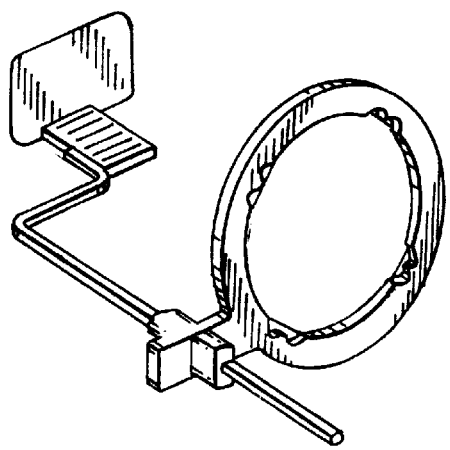

FIGS. 2A and 2B illustrate two examples of the color coding method and apparatus of the present invention for color coding the components of the dental X-ray. More specifically, FIG. 2A illustrates an interior positioning system wherein the components thereof are color coded for X-raying interior dental areas. In FIG. 2B, a posterior positioner is illustrated with components color coded for X-raying posterior dental areas of the patient. It will be appreciated that the colors chosen may be any combination of colors.

Figure 3A:
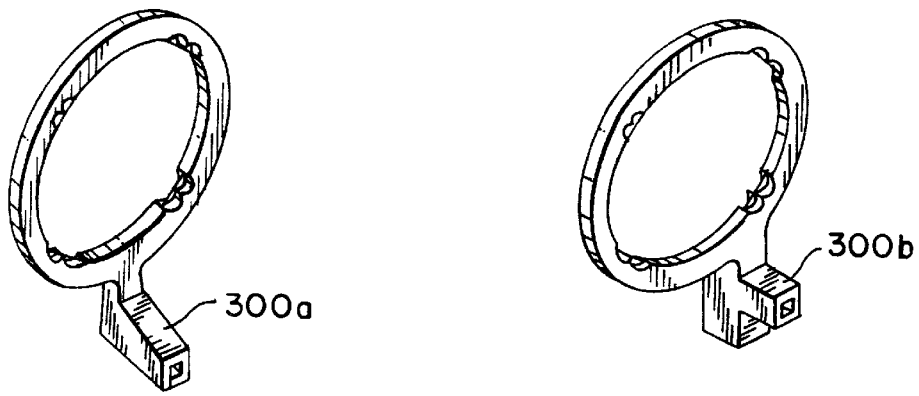
FIGS. 3A–3D illustrate anterior and posterior components of the present invention.
Figure 3B:
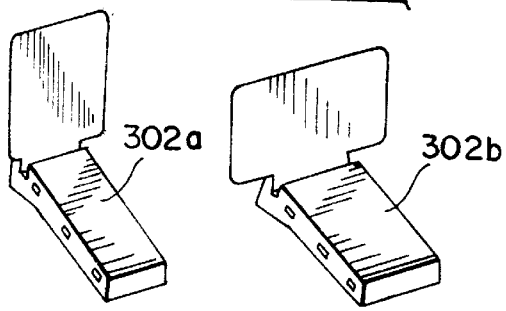

FIG. 3A illustrates the anterior and posterior aiming rings. As will be appreciated, the anterior aiming ring is constructed with a holding member 300a for holding an anterior arm such that the anterior bite-block and X-ray film thereon are directed to the optimum position and alignment for X-raying the anterior dental area of the patient's teeth. In the figure illustrated, the holding member 300a of the anterior aiming ring is directed away from the longitudinal axis of the anterior aiming ring and is extended in the approximate direction of the X-ray beam. The posterior aiming ring by contrast, includes a holding member 300b which is constructed for holding a posterior arm at the optimum position such that the posterior bite-block and X-ray film thereon are placed at the optimum position and alignment for X-raying posterior areas of the patient's teeth. As illustrated in FIG. 3B, the holding member 300b is closer to the longitudinal axis of the posterior aiming ring and is truncated in the direction of the X-ray beam as compared with the anterior aiming ring. It will be appreciated that the particular arrangements of the anterior and posterior aiming rings may vary according to the desired dental area to be X-rayed.

FIG. 3B illustrates the anterior bite-block 302a for holding anterior X-ray films at the anterior of the dental area of the patient's mouth and the posterior bite-block 302b for holding posterior X-ray films at the posterior of the patient's mouth. As illustrated in FIG. 3B, the anterior bite-block is constructed in a more narrow and elongated arrangement which is optimum for X-raying anterior dental areas of the patient's teeth. By contrast, the posterior bite-block is constructed wider and more stout which is optimum for X-raying posterior dental areas of the patient's teeth.

Figure 3C:
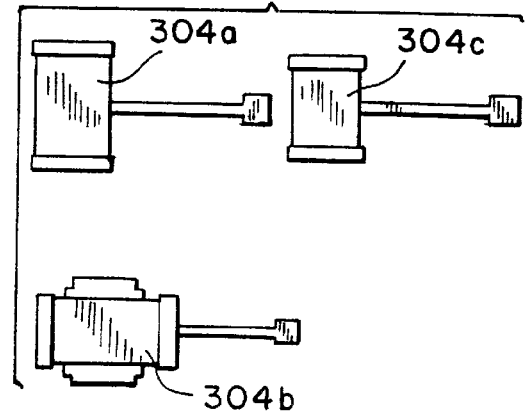

FIG. 3C illustrates bite-wing blocks 304 *a, b, c* of the present invention which are employed for X-raying the opposing coronal area, known as the head or crown. As illustrated in FIG. 3C, the bite-wing blocks are provided in different configurations which correspond to different opposing coronal areas.

Figure 3D:
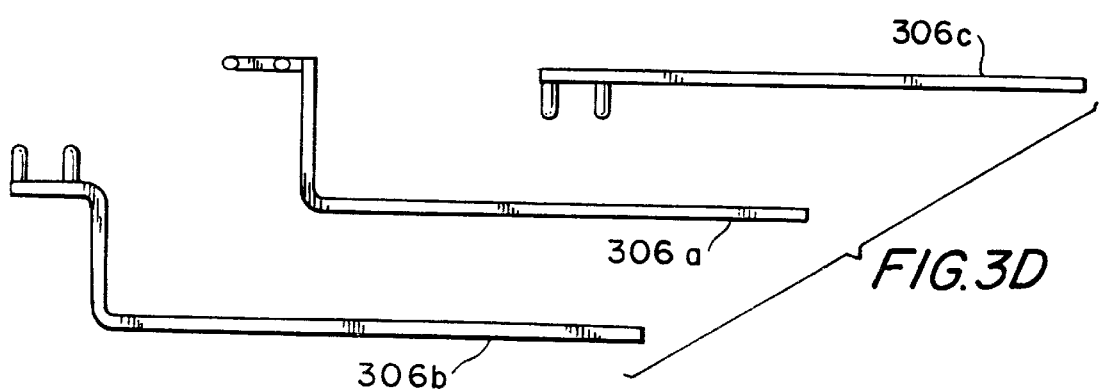

FIG. 3D illustrates the anterior arm 306a, the posterior arm 306b and the bitewing arm 306c which couple respective aiming rings to the bite-blocks. As illustrated in FIG. 3D, the indicator arms are constructed to obtain, in combination with the respective aiming ring, the optimum position and alignment for positioning the respective bite-block and X-ray film thereon in the particular dental area to be X-rayed. In particular, the posterior arm is configured such that, in combination with the posterior aiming ring and posterior bite-block, the dentist achieves optimum position and alignment of the posterior X-ray film for X-raying the posterior dental area. Similarly, the anterior arm is configured such that, in combination with the anterior aiming ring and anterior bite-block, the dentist achieves the optimum position and alignment for the anterior X-ray film for X-raying the anterior dental area. The bite-wing arm is configured such that the dentist achieves the optimum position and alignment for X-raying the opposing coronal area.

The present invention provides quick and easy assembly of the aiming rings, bite-blocks and indicator arms by color coding at least one of these components. In the preferred embodiment, the aiming rings and bite-blocks are color coded. For example, the anterior aiming ring and the anterior bite-block are color coded green whereas the posterior aiming ring and the posterior bite-block are color coded orange. With this arrangement, it is relatively simple for the dentist or dental technician to identify by the color coding scheme of the present invention the correct aiming ring and corresponding bite-block. Of course, it will be appreciated that other colors may be chosen for representing the components of the positioner of the present invention.

In the embodiment illustrated in the figures, the indicator arms are not color coded. However, it will be appreciated that the indicator arms as well may be color coded. For example, the posterior arm in the foregoing example may be color coded orange while the anterior arm may be color coded green.

In another embodiment, the bite-wing blocks are also color coded. For example, and as shown in the Figures, the bite-wing blocks are color coded white. Of course, the bite-wing blocks may be color coded to any color. With this arrangement, the dentist or dental technician will not confuse the bite-wing blocks with the bite-blocks.

In operation, the color coding scheme of the present invention provides the dentist or dental technician with the capability to quickly and easily assemble all the interchangeable parts of the positioner according to the color coding thereby resulting in the optimum position and alignment for X-raying the particular dental area. As shown in FIG. 2A, for example, the dentist quickly and easily assembles the color coded anterior bite-block, the anterior arm and the anterior aiming ring according to the color coding scheme which matches the colors of one or more components in the anterior positioner. FIG. 2B, for example, illustrates that the posterior positioner is assembled quickly and easily by color coding one or more of the posterior aiming ring, the posterior bite-block and the posterior arm. The present invention, in particular, is effective for providing the optimum position and alignment for dental-X-raying the following regions: Maxillary Incisor, Maxillary Lateral Incisor, Maxillary Cuspid, Maxillary Bicuspid (Premolar), Maxillary Molar, Mandibular Incisor, Mandibular Cuspid, Mandibular Bicuspid (Premolar), Mandibular Molar, Interproximial Bicuspid (Premolar) and Interproximial Molar. Although, other regions of the mouth are certainly within the scope of the present invention.

Figure 4A:
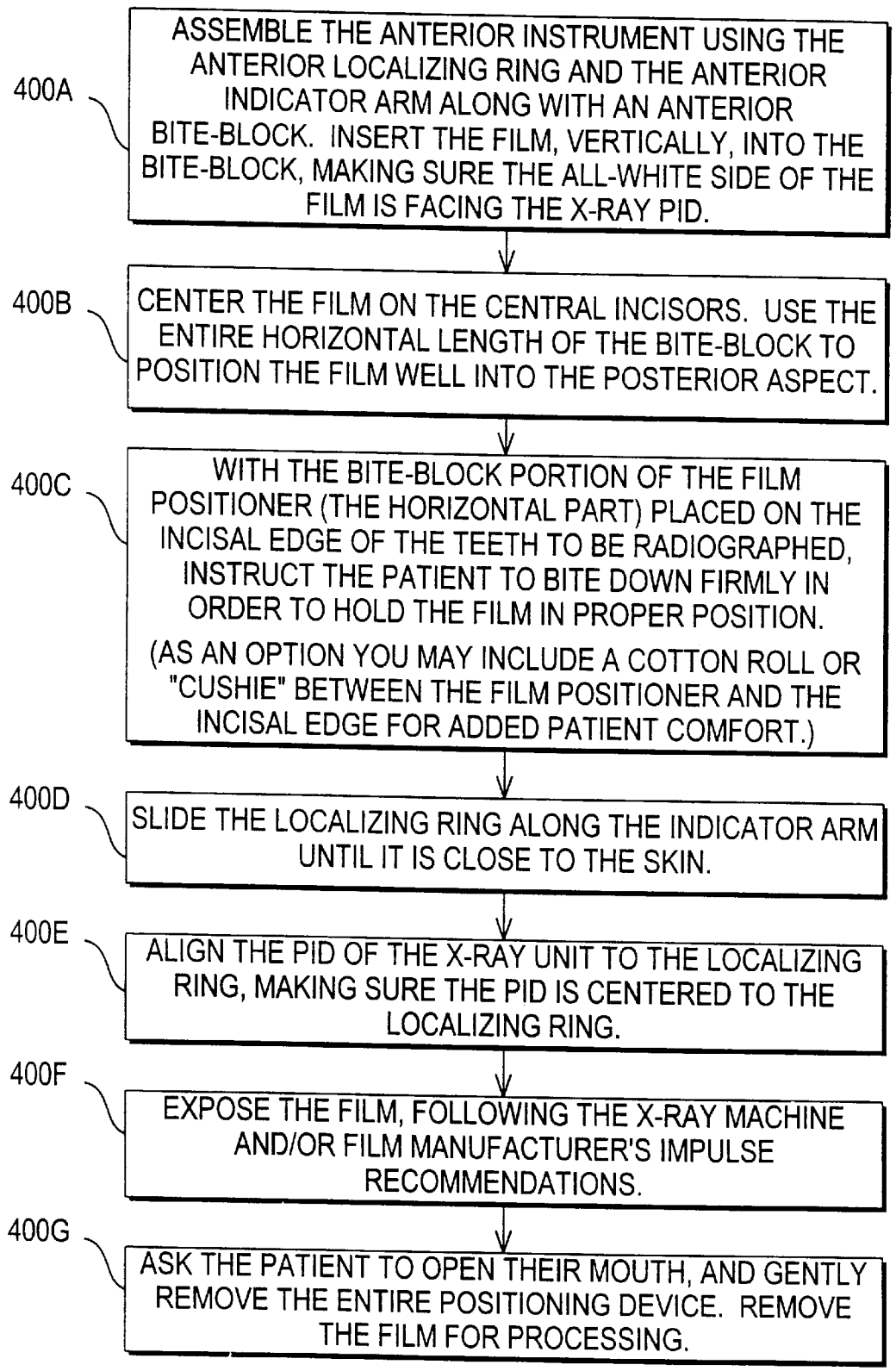

A method for employing the color coding scheme of the present invention will now be described for each of the aforementioned regions. For X-raying the maxillary incisor region, reference to FIGS. 4A–C is made. As illustrated by the flowchart of FIG. 4A, the operator assembles the anterior positioner using the anterior localizing ring 402 and the anterior indicator arm 406 along with the anterior bite-block 404. The film is inserted vertically into the bite-block with the all-white side of the film facing the X-ray PID. Although FIG. 4B shows that the anterior localizing ring and the anterior bite-block are color coded, it will be appreciated that one or more of the components shown in FIG. 4B may be color coded. In step 400B, the operator centers the film on the central incisors 408 as shown in FIG. 4C. It is preferred that the entire horizontal length of the bite-block is used to position the film well into the posterior aspect 410 as shown in FIG. 4C. In step 400C, with the bite-block portion of the film positioner (the horizontal part) placed on the incisal edge of the teeth to be radial graphed, the operator instructs the patient to bite down firmly 412 in order to hold the film in proper position. In the alternative, a cotton roll or "cushie" between the film positioner and the incisal edge for added patient comfort may be provided. The operator in step 400D slides the localizing ring along the indicator arm until it is close to the skin of the patient. In step 400E, the operator aligns the PID of the X-ray unit to the localizing ring, making sure that the PID is centered to the localizing ring. The operator, in step 400F, exposes the film, following the X-ray and/or film manufacturer's impulse recommendations. In step 400G, the operator asks the patient to open their mouth, and gently removes the entire positioning device. The X-ray film is removed for processing. Examples of the developed X-ray film is indicated by the negatives 414 shown in FIG. 4C.

Figure 5A:
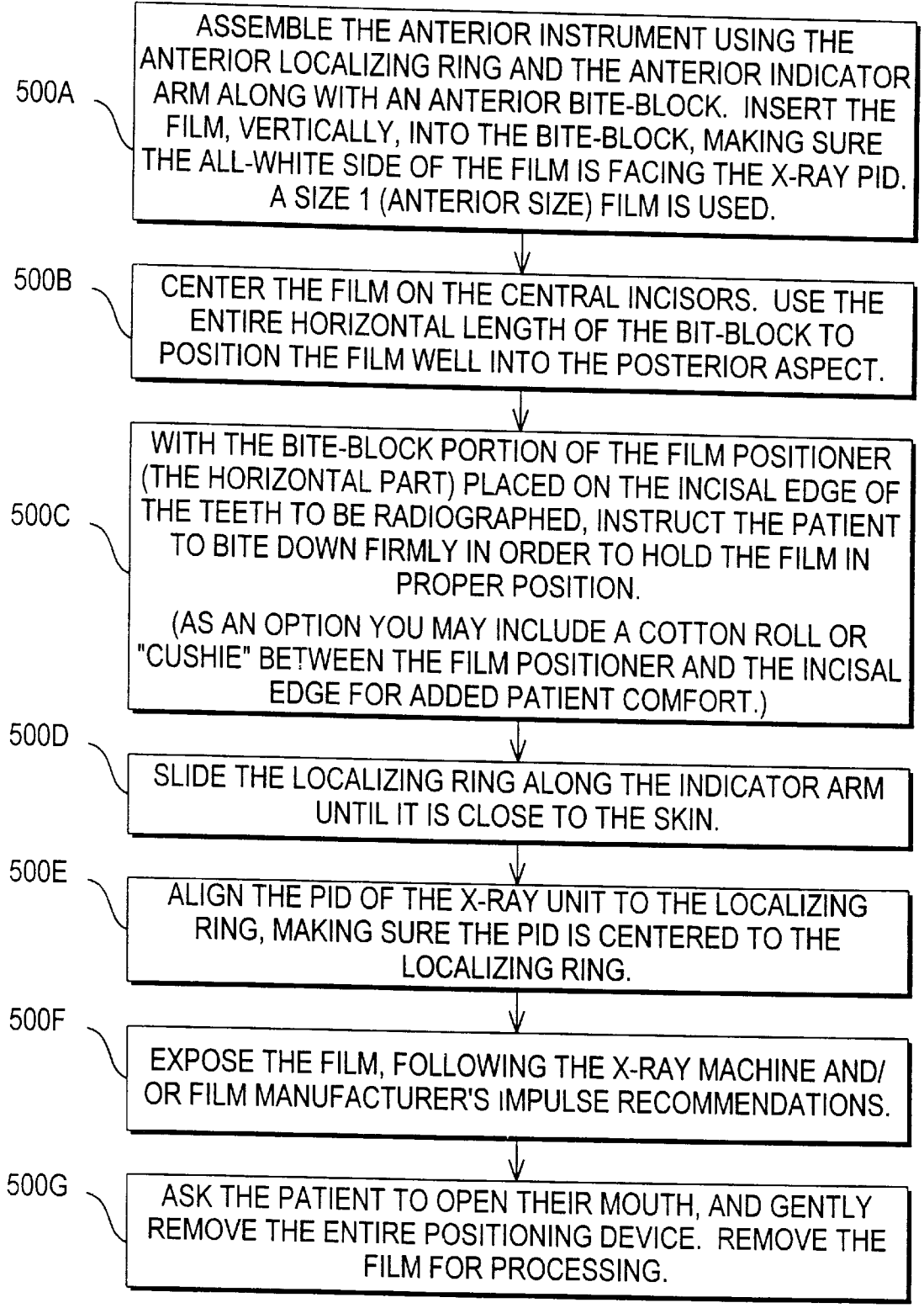

FIGS. 5A–C illustrate the method of X-raying the maxillary lateral incisor region according to the present invention. In this case, steps 500A–G are similar to those shown in FIG. 4A except that the operator positions the positioner of the present invention to X-ray the maxillary lateral incisor region 510 shown in FIG. 5C. In summary, the operator assembles the anterior localizing ring 502, the anterior bite-block 504 and the anterior arm 506 shown in FIG. 5B. It is preferable that the size of the X-ray film used is of size 1 (anterior size), however, the X-ray film may, of course, vary according to the needs of the operator. The operator thus, positions the X-ray film proximate to the maxillary lateral incisor region 508 as shown in FIG. 5C by adjusting, for example as shown by reference numeral 512, resulting in the exemplary negatives 514 shown in FIG. 5C.

The method for X-raying the maxillary cuspid region is illustrated in FIGS. 6A–C. In step 600A, the operator assembles the anterior positioner of the present invention using the anterior localizing ring 602 and the anterior indicating arm 606 along with an anterior bite-block 604. The operator, then, inserts the film vertically into the bite-block, making sure the all-white side of the film is facing the X-ray PID. Typically, a size 1 (anterior size) film is required but, of course, other size films such as a size 2 (adult size periapical) film may be used. The film may require shaping, such as curling the anterior corner slightly to aid in the positioning of the instrument. In step 600B, the operator positions the film with the cuspid and the first bicuspid centered on the film. It is preferred that the entire horizontal length of the bite-block is used to position the film well into the posterior aspect. Steps 600C–G are similar to the previously described steps of FIG. 4A and a description thereof is referred thereto. In this case, the dentist assembles the anterior localizing ring 602, the anterior bite-block 604 and the anterior arm 606 as shown in FIG. 6B and positions the film proximate to the maxillary cuspid region 608, 610 and 612 which results in the exemplary negatives 614 shown in FIG. 6C.

FIGS. 7A–C illustrate the method for X-raying the maxillary bicuspid (premolar) region 708 shown in FIG. 7C. As shown in FIG. 7A, the operator assembles the posterior positioner of the present invention using the posterior localizing ring 702, the posterior indicator arm 706 and the posterior bite-block 704 shown in FIG. 7B. The operator inserts the film vertically into the bite-block, making sure that the all-white side of the film is facing the X-ray PID. It may be necessary to curl the upper anterior corner slightly to aid in positioning the instrument. In step 700B, the film is centered on the second bicuspid, for example, using the entire horizontal length of the bite-block to position the film well in the mid-palatial aspect 710 as shown in FIG. 7C. Steps 700C–G are similar to steps 400C–G and a description is found in the corresponding sections of the specification. With this method, the operator positions the positioner of the present invention as shown in reference numeral 712 in FIG. 7C resulting in the developed X-ray negative example 714 shown in FIG. 7C.

Figure 8A:
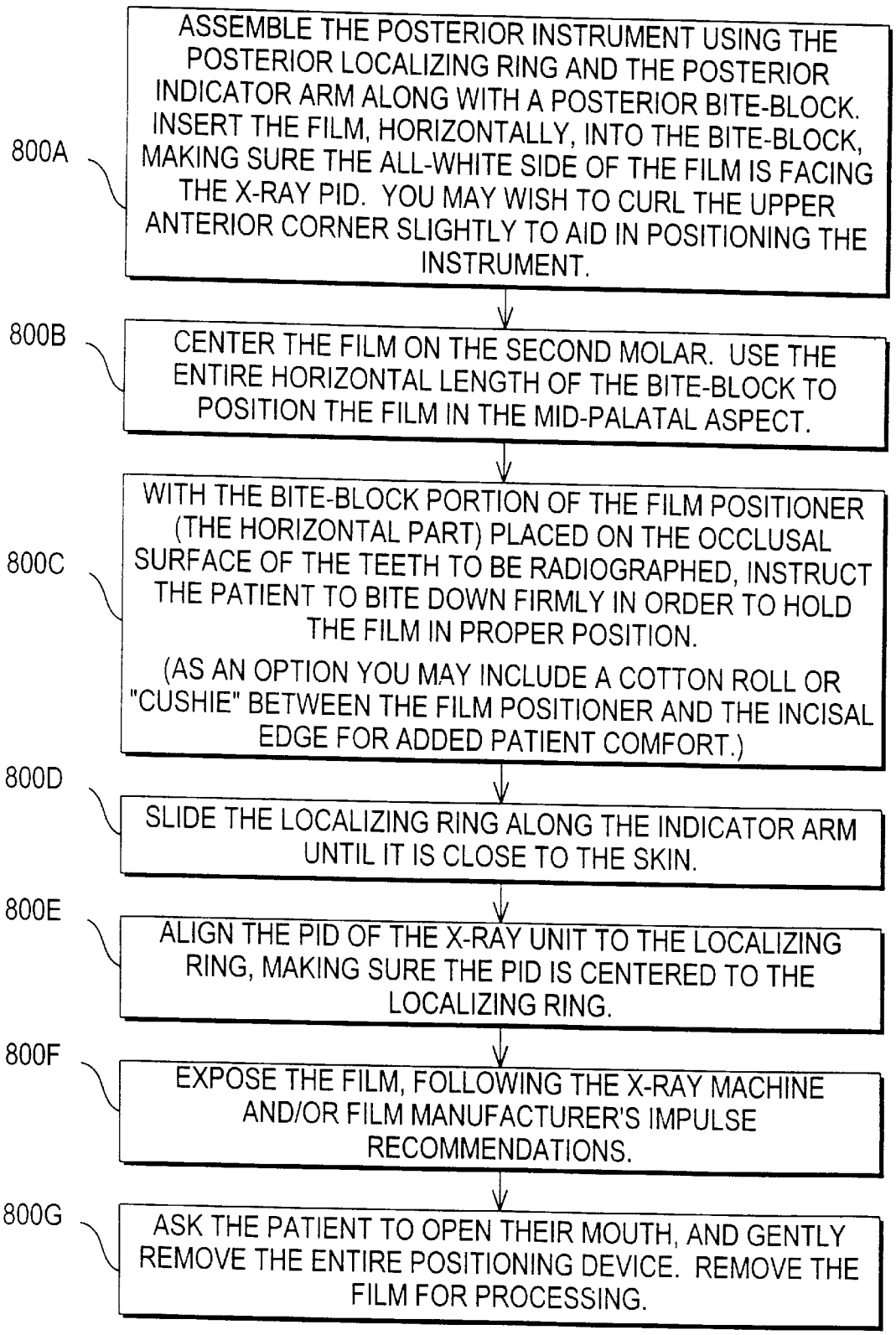
FIGS. 8A–8C illustrate the method for X-raying the maxillar molar region.
Figure 8B:
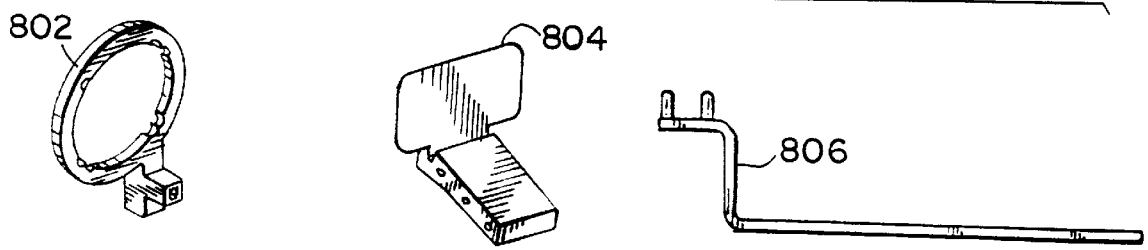
Figure 8C:
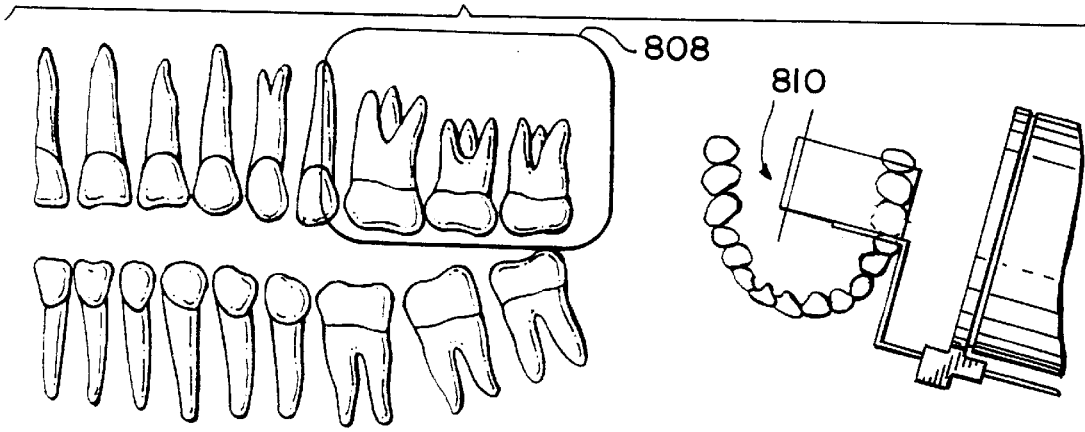
Figure 8C:
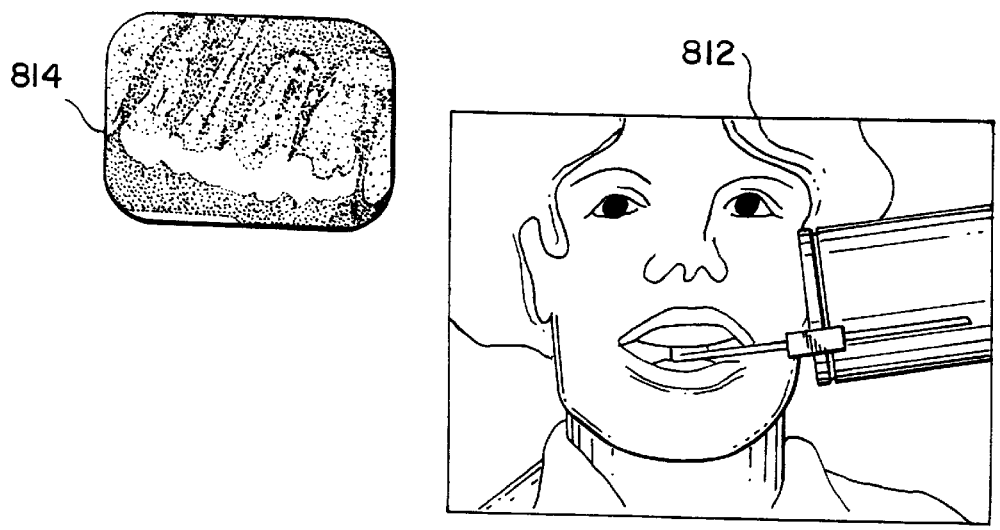

The method for X-raying the maxillary molar region is illustrated in FIGS. 8A–C. In FIG. 8A, the operator in step 800A assembles the posterior positioner of the present invention using the posterior localizing ring 802, the posterior indicator arm 806 and the posterior bite-block 804. The film is inserted horizontally into the bite-block making sure that the all-white side of the film is facing the X-ray PID. It may be necessary to curl the upper anterior corner slightly to aid in the positioning of the instrument. In step 800B, the film is centered on a second molar 808 as shown in FIG. 8C using the entire horizontal length of the bite-block to position the film in the mid-palatal aspect 810. Steps 800C–G are similar t6 400C–G and the description thereof is referred to the corresponding sections of the specification. With this method, the operator positions the position of the present invention as shown in 812 resulting in the X-ray negative example 814 shown in FIG. 8C.

Figure 9A:
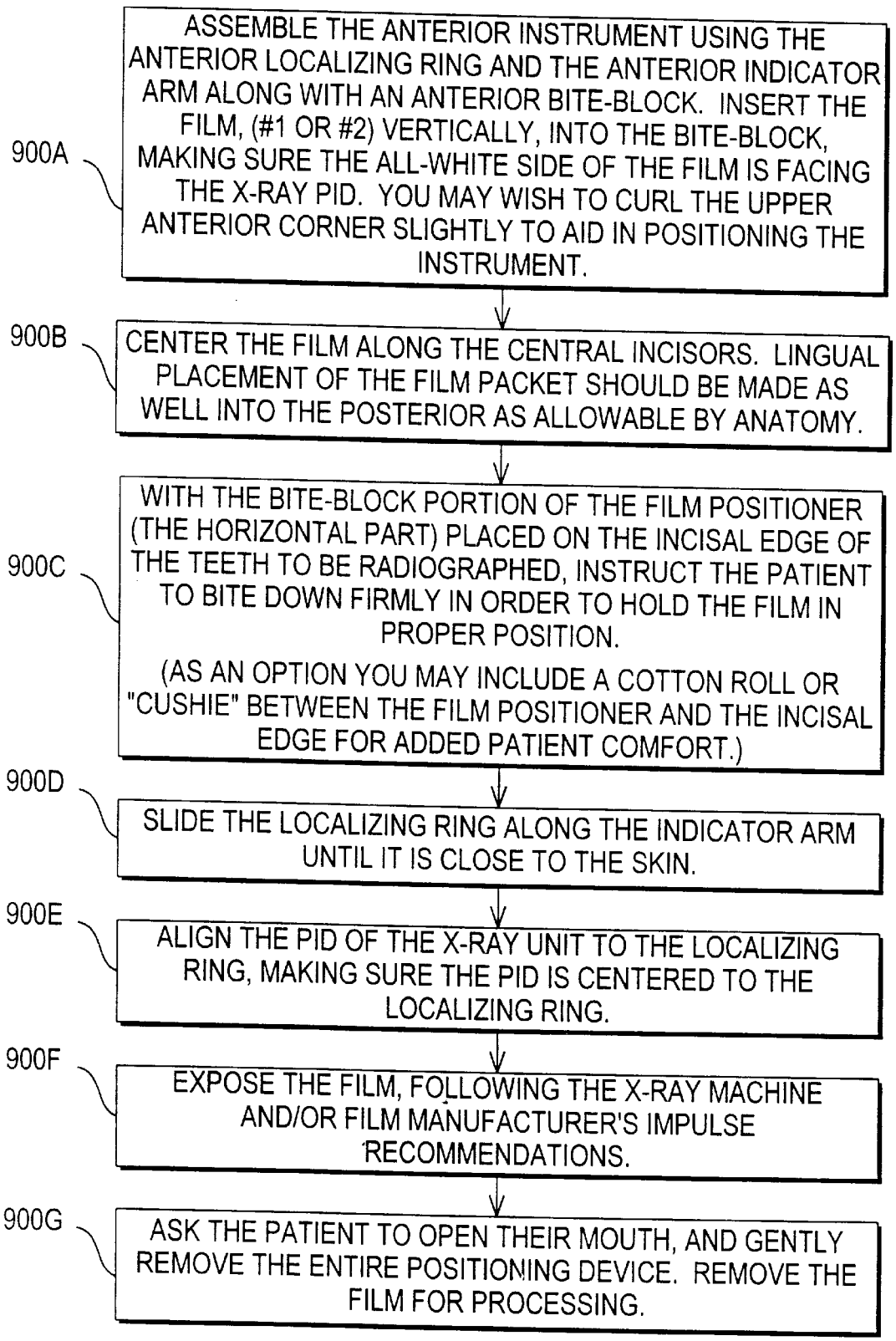
FIGS. 9A–9C illustrate the method for X-raying the mandibular incisor region.
Figure 9B:
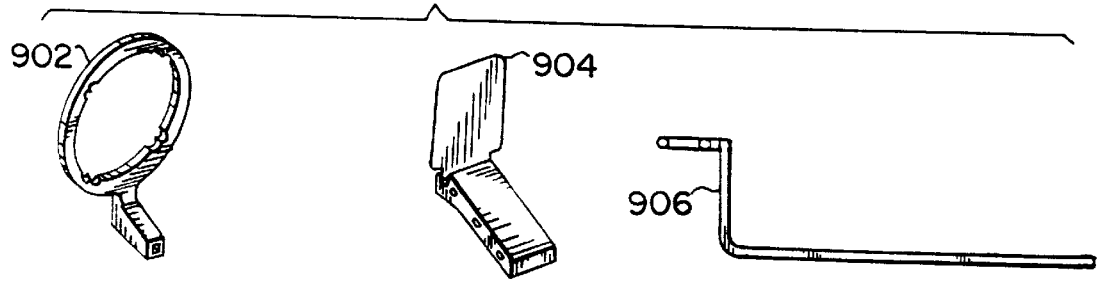
Figure 9C:
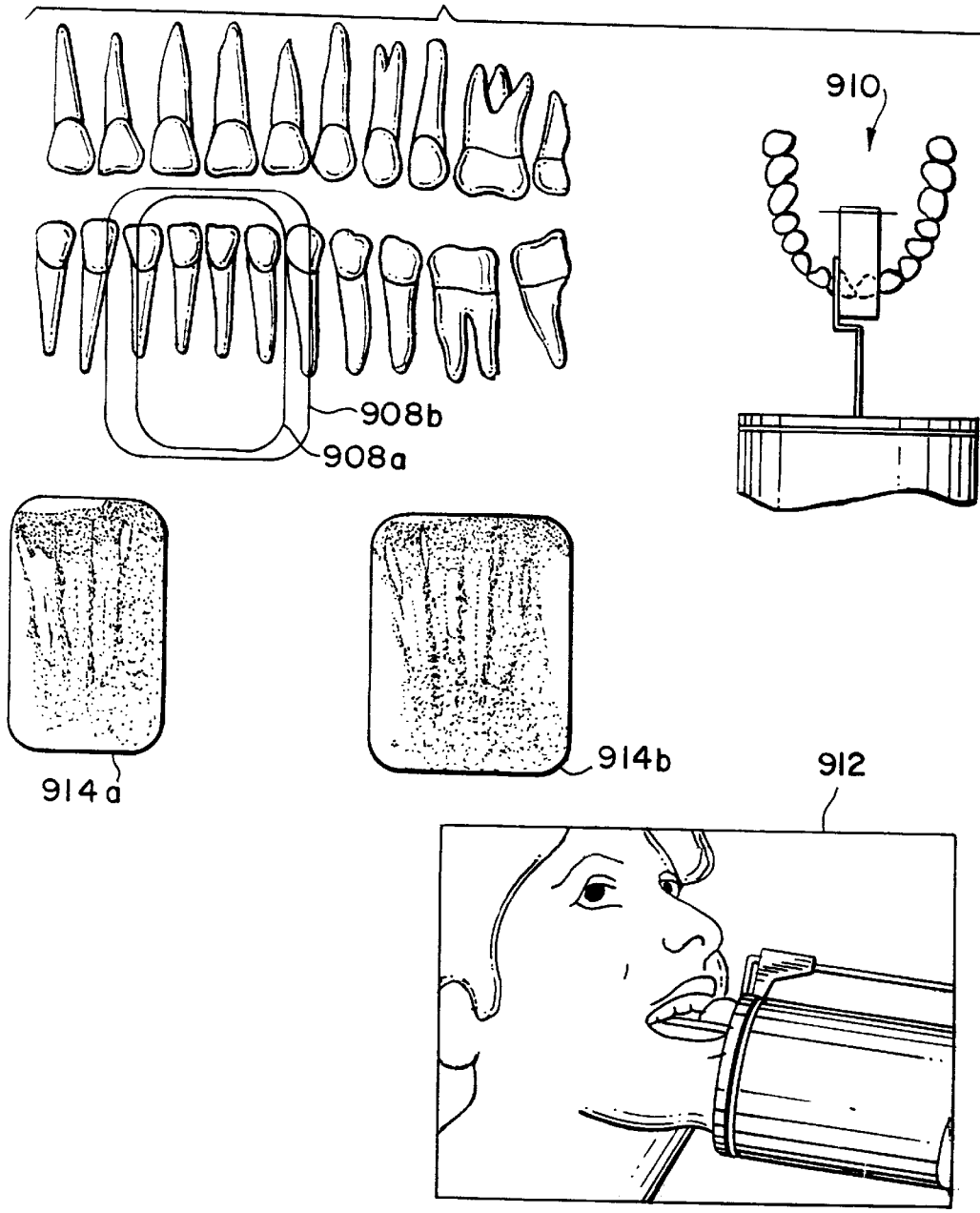

The method for X-raying the mandibular incisor region 908 is illustrated in FIGS. 9A–C. As shown in FIG. 9A, in step 900A, the operator assembles the anterior positioner of the present invention using the anterior localizing ring 902 and the anterior indicator arm 906 with an anterior bite-block 904. The film (number 1 or 2 size) is inserted vertically into the bite-block with the all-white side of the film facing the X-ray PID. It may be necessary to curl the upper anterior corner slightly to aid in positioning the instrument of the present invention. In step 900B, the operator centers the film along the central incisors 908. Lingual placement of the film packet is preferably made as well into the posterior as allowable by the anatomy of the patient as shown in 910 of FIG. 9C. With the bite-block of the film positioner (horizontal part) placed on the incisal edge of the teeth to be radial graphed, the patient is instructed to bite down firmly 912 in order to hold the film in proper position. Steps 900D–G are similar to 400D–G and the description thereof is referred to the corresponding sections of the specification. With this X-raying method of the present invention, the exemplary X-ray negatives 914 of the mandibular incisor region are produced.

Figure 10A:
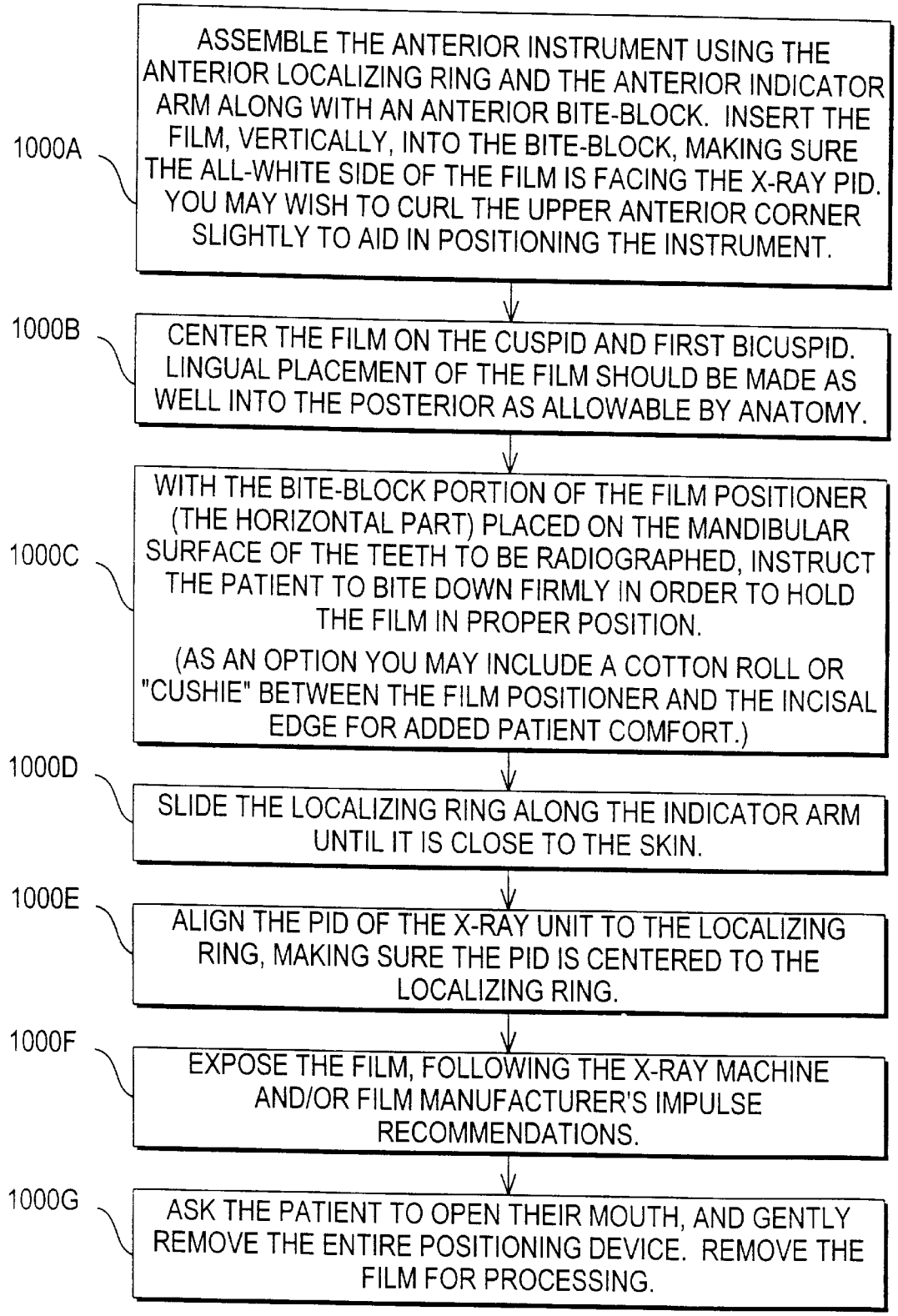
FIGS. 10A–10C illustrate the method for X-raying the mandibular cuspid region.
Figure 10B:
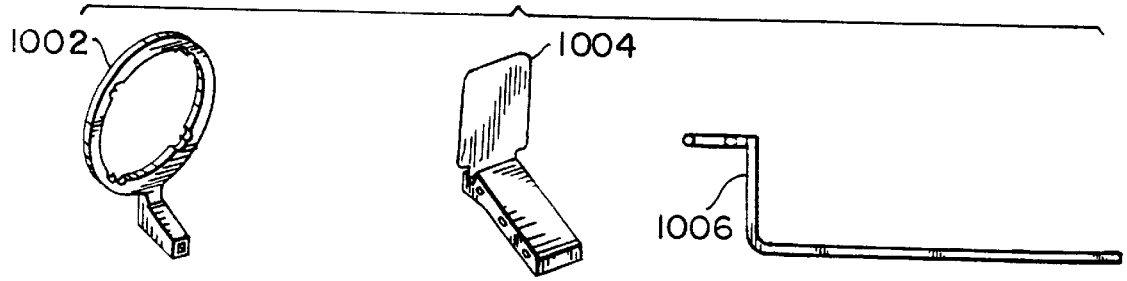
Figure 10C:
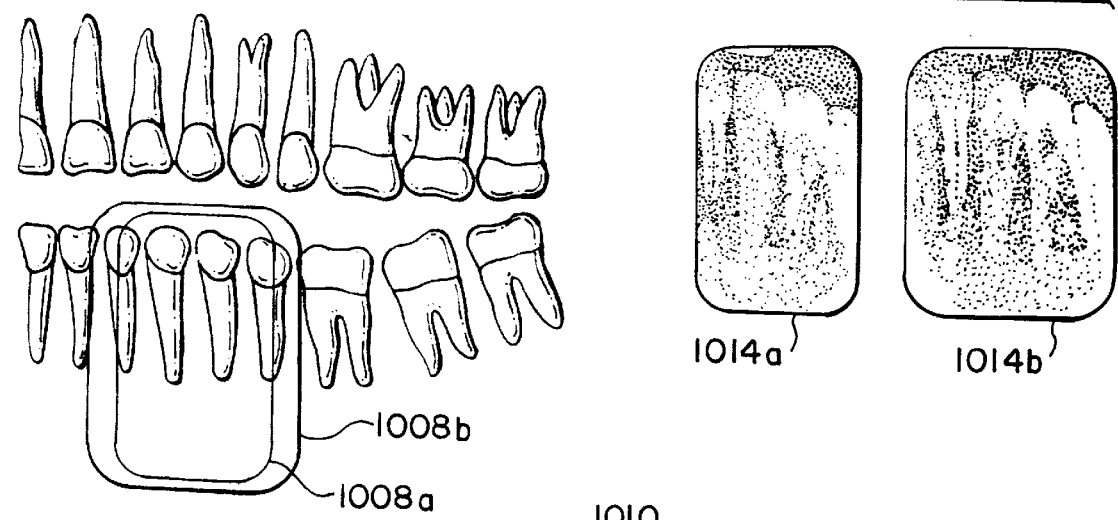
Figure 10C:
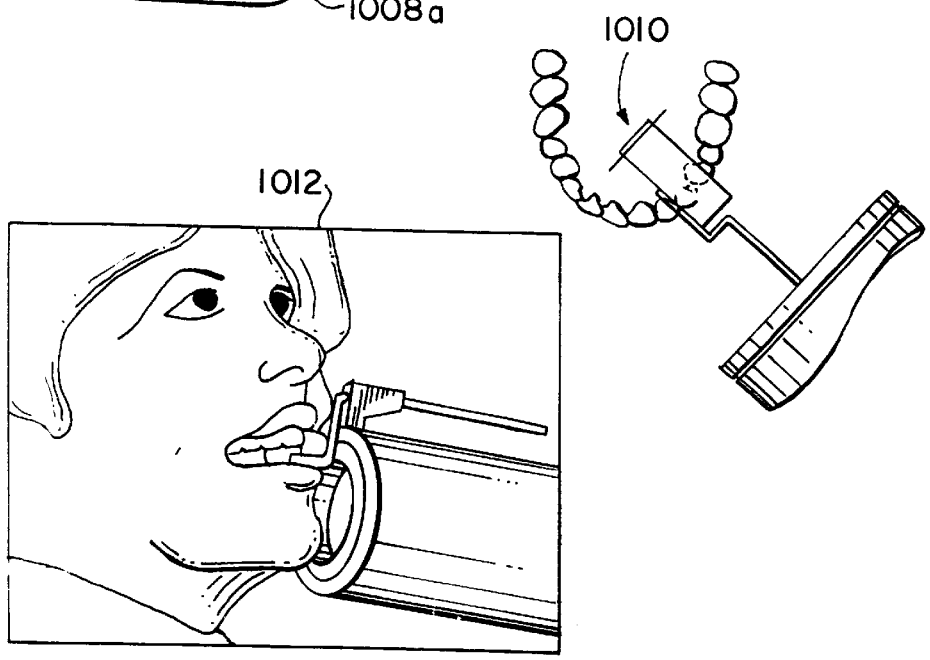

The method for X-raying the mandibular cuspid region 1008 is illustrated in FIGS. 10A–C. In FIG. 10A, in step 1000A the operator assembles the anterior positioner of the present invention using the anterior localizing ring 1002 and the anterior indicator arm 1006 with the anterior bite-block 1004. The film is inserted vertically into the bite-block with the all-white side of the film facing the X-ray PID. It may be necessary to curl the upper anterior corner slightly to aid in the positioning of the instrument of the present invention. In step 1000B, the film is centered on the cuspid and first bicuspid 1008 as shown in 1010 of FIG. 3C. Lingual placement of the film should be made as well into the posterior as allowable by the patient's anatomy 1010. In step 1000C, with the bite-block of the film positioner (the horizontal portion) placed on the mandibular surface of the teeth to be radial graphed, the patient is instructed to bite down firmly 1012 in order to hold the film in proper position. Since steps 1000D–G are similar to 400D–G, a description thereof is referred to the corresponding sections of the specification. With the method of the present invention, the exemplary X-ray negatives 1014 shown in FIG. 10C are developed.

Figure 11A:
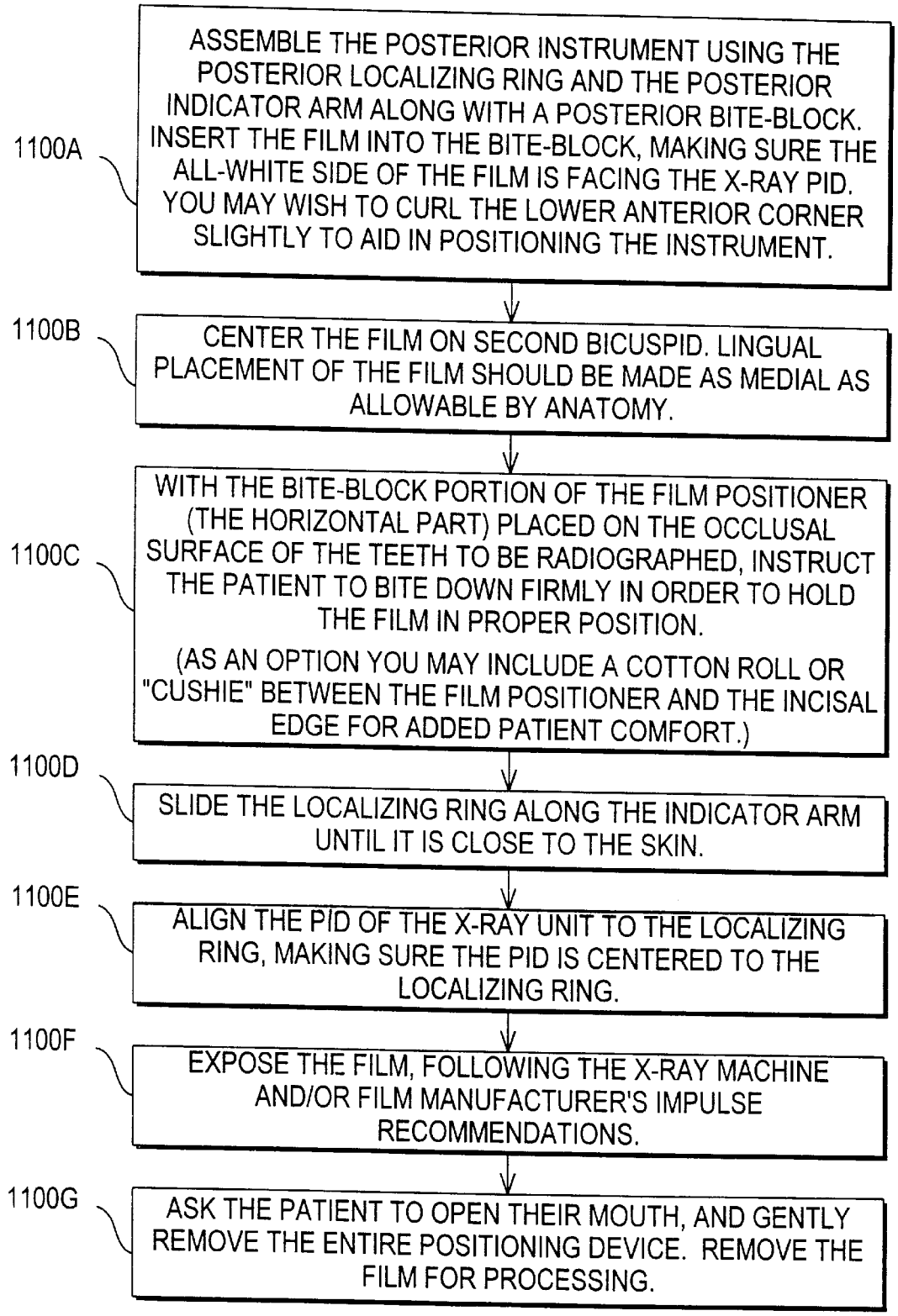

The method for X-raying the mandibular bicuspid (premolar) region 1108 is illustrated in FIGS. 11A–C. In step 1200A, the operator assembles the posterior positioner of the present invention using the posterior localizing ring 1102, the posterior indicator arm 1106 and the posterior bite-block 1104. The film is inserted into the bite-block with the all-white side of the film facing the X-ray PID. It may be necessary to curl the lower anterior corner slightly to aid in the positioning of the instrument. In step 1100C, with the bite-block portion of the film positioner (the horizontal portion) placed on the occlusal surface of the teeth to be radial graphed, the patient is instructed to bite down firmly in order to hold the film in proper position as shown in 1112 of FIG. 11C. Steps 1100D–G are similar to 400D–G and a detailed description thereof is referred to the corresponding section of the specification. With the X-ray method of the present invention, the exemplary X-ray negative 1114 shown in FIG. 11C is developed.

Figure 12A:
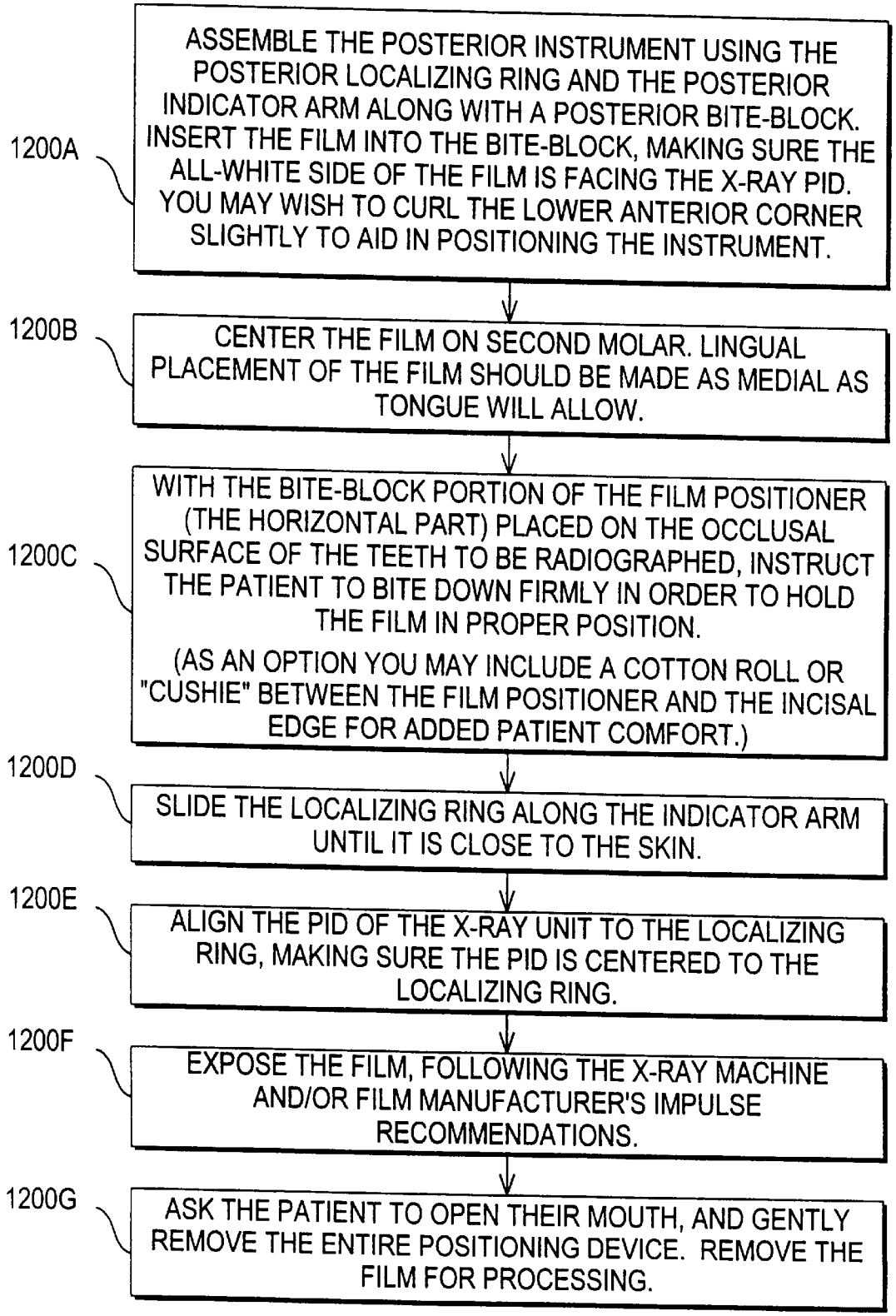
FIGS. 12A–12C illustrate the method for X-raying the mandibular molar region.
Figure 12B:
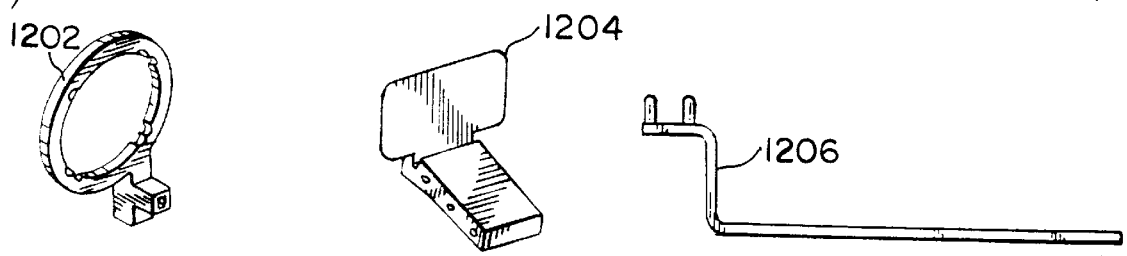
Figure 12C:
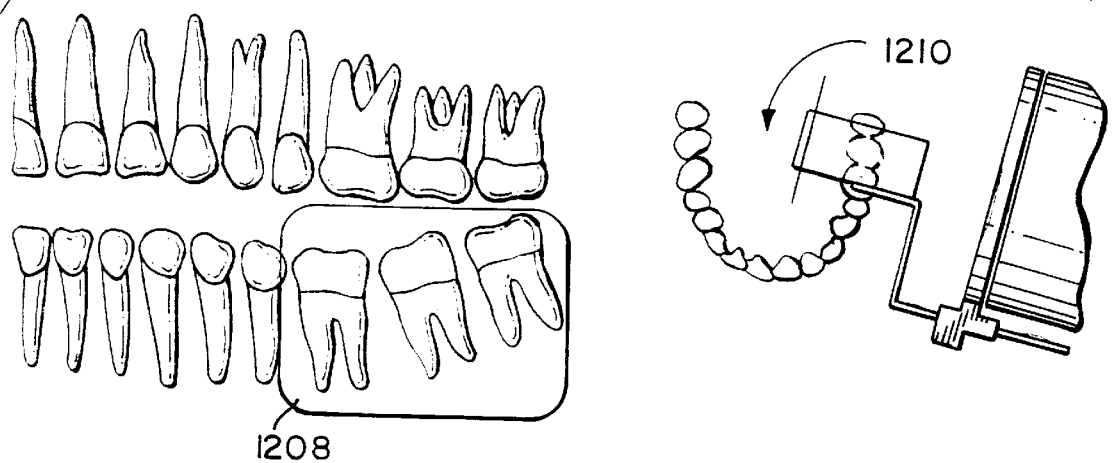
Figure 12C:
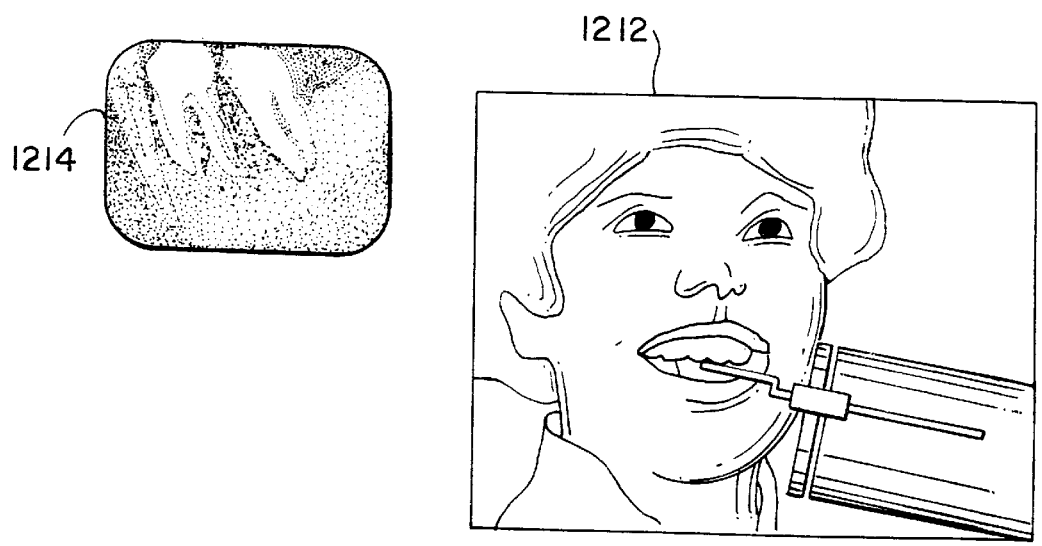

The method for X-raying the mandibular molar region 1208 of the present invention is illustrated in FIGS. 12A–C. In step 1200A, the operator assembles the posterior positioner of the present invention using the posterior localizing ring 1202 and the posterior indicator arm 1206 along with the posterior bite-block 1204. The film is inserted into the bite-block with the all-white side of the film facing the X-ray PID. It may be necessary to curl the lower interior corner slightly to aid in positioning the instrument. In step 1200B, the film is centered on the second molar 1208. Lingual placement of the film should be made as medial as the tongue of the patient will allow. In step 1200C, the bite-block portion of the film positioner (the horizontal portion) is placed on the occlusal surface of the teeth to be radial graphed as shown by 1210 and the patient is instructed to bite-down firmly in order to hold the film in proper position as shown in 1212 of FIG. 12C. The steps 1200D–G are similar to steps 400D–G of FIG. 4A and a description thereof is referred to the corresponding sections of the specification. With the method of the present invention, the exemplary X-ray negative 1214 is developed.

Figure 13A:
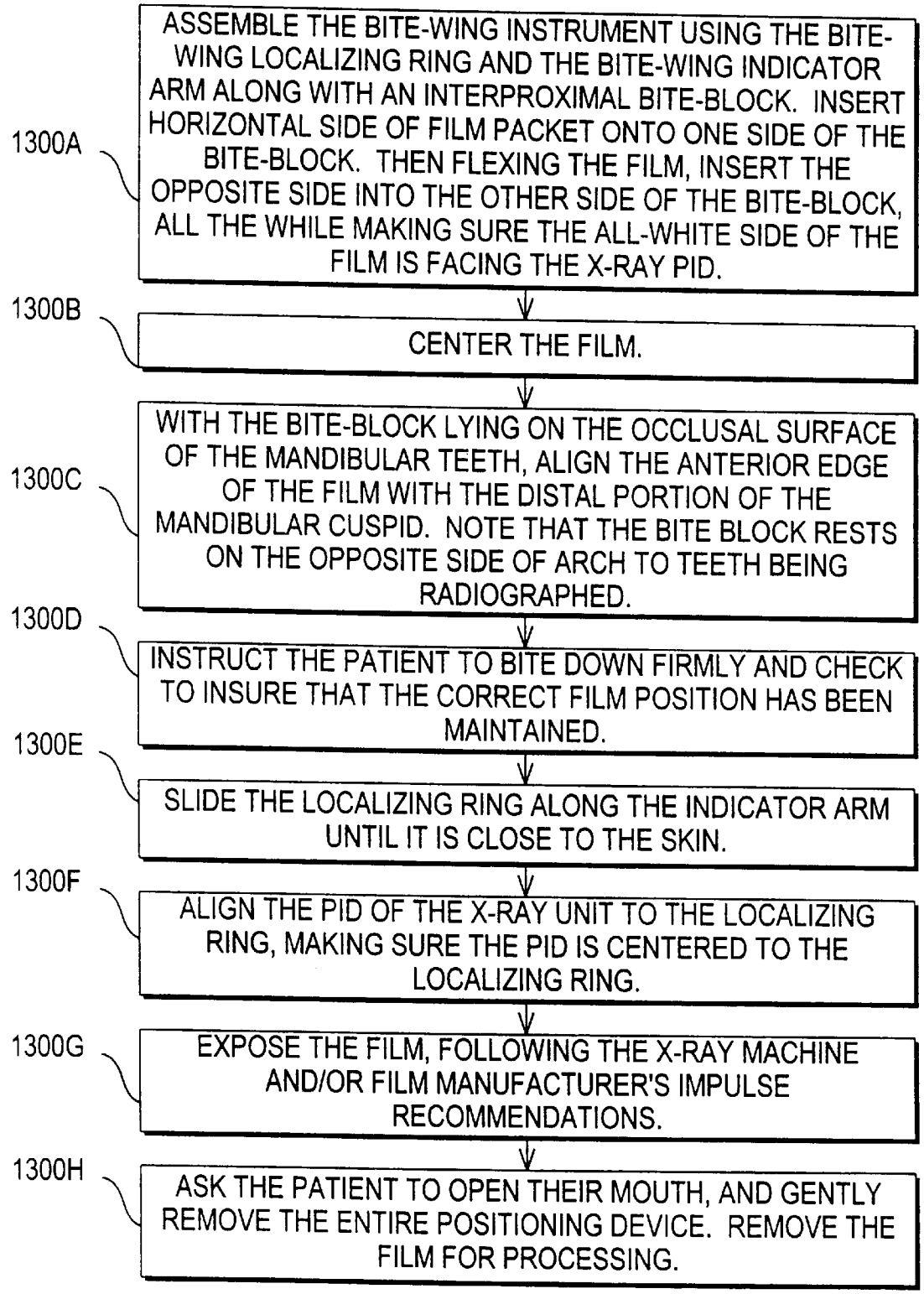
FIGS. 13A–13C illustrate the method for X-raying the interproximal bicuspid (premolar) region.
Figure 13B:
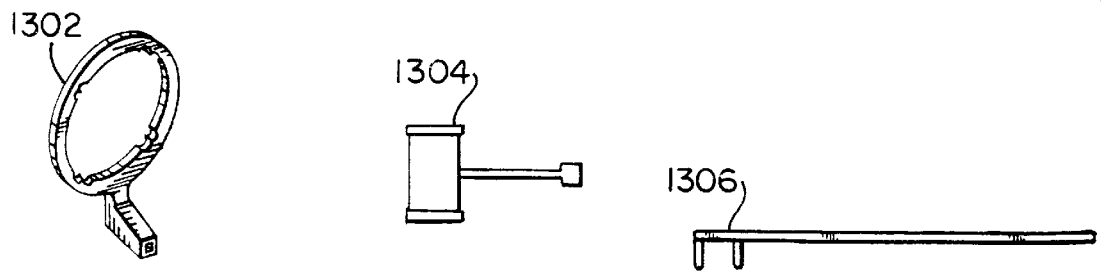
Figure 13C:
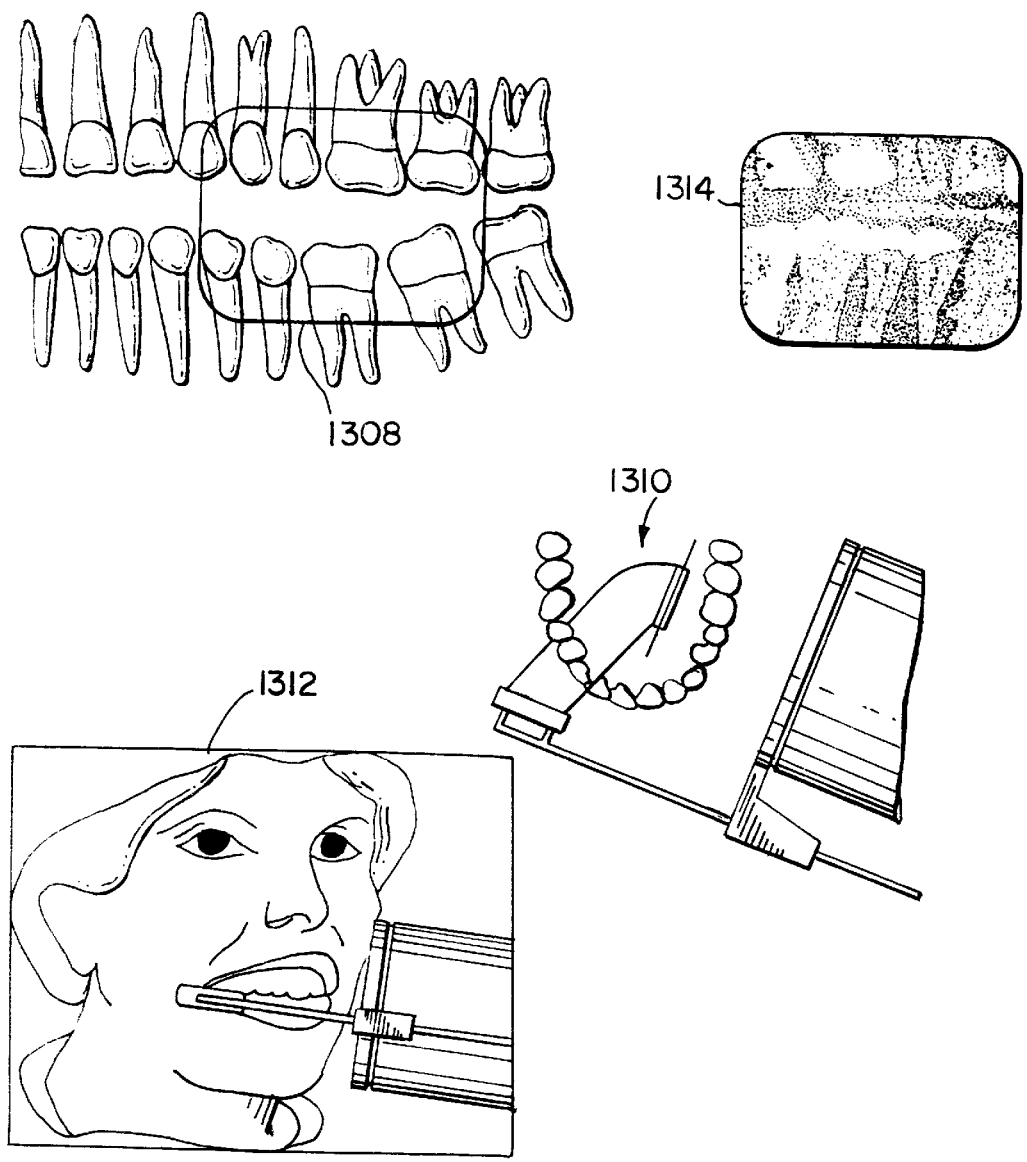

The method for X-raying the interproximal bicuspid (premolar) region 1308 is illustrated in FIGS. 13A–C. In step 1300A, the operator assembles the bite-wing positioner of the present invention using the bite-wing localizing ring 1302, the bite-wing indicator arm 1306 and the interproximal bite-block 1304. The horizontal side of the film packet is inserted onto one side of the bite-block. Then, by flexing the film, the film is inserted into the opposite side into the other side of the bite-block making sure that the all-white side of the film is facing the X-ray PID. The operator centers the film in step 1300B. In step 1300C, the bite-block lying on the occlusal surface of the mandibular teeth, align the interior edge of the film as shown in 1310 of FIG. 13C with the distal portion of the mandibular cuspid. It is preferred that the bite-block rests on the opposite side of the arch to the teeth being radial graphed. In step 1300D, the patient is instructed to bite-down firmly and check to insure that the correct film position has been maintained ass shown by 1312 of FIG. 13C. In step 1300E, the operator slides the localizing ring along the indicator arm until it is close to the skin. In 1300F, the PID of the X-ray unit is aligned to the localizing ring, making sure that the PID is centered to the localizing ring. In step 1300G, the film is exposed following the X-ray machine and/or film manufacturer's impulse recommendations. In step 1300H, the patient is asked to open their mouth and gently remove the entire positioning device and the film is removed for processing. With the method of the present invention, the exemplary X-ray negative 1314 is developed.

Figure 14A:
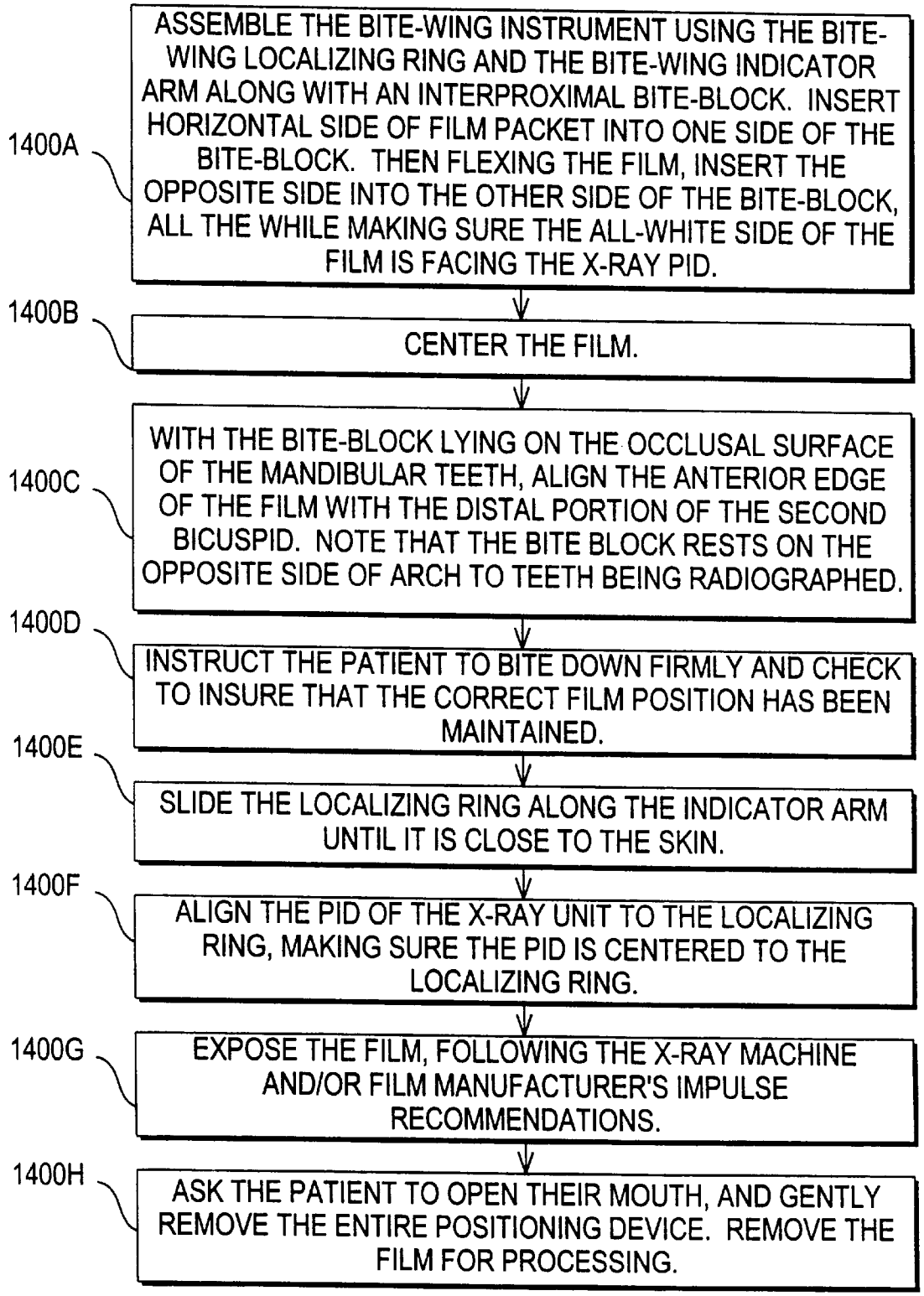
FIGS. 14A–14C illustrate the method for X-raying the interproximal molar region.
Figure 14B:
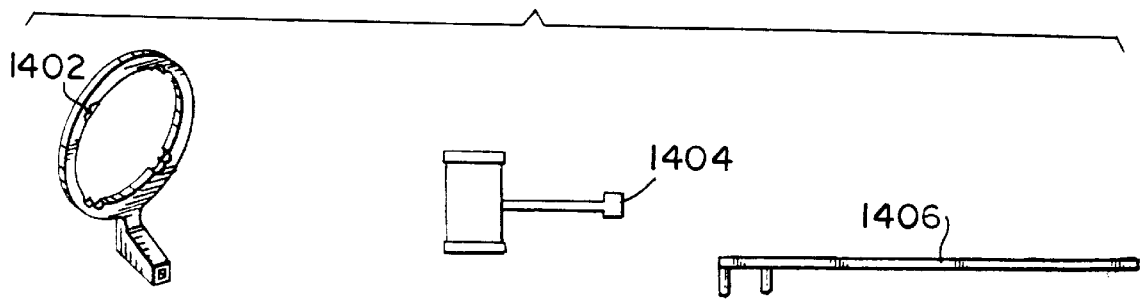
Figure 14C:
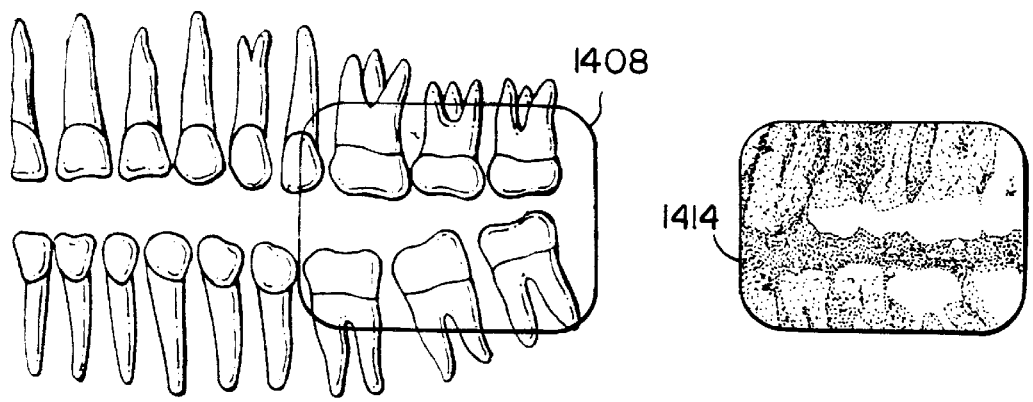
Figure 14C:
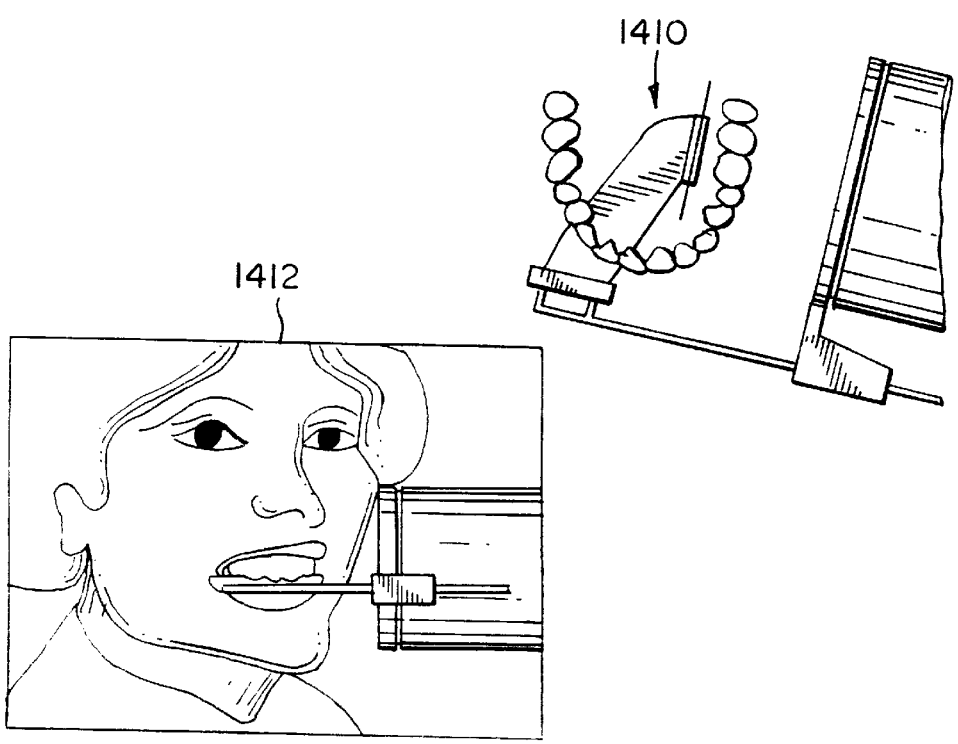

The method of X-raying the interproximal molar region 1408 is illustrated in FIGS. 14A–B. In step 1400A, the operator assembles the bite-wing positioner instrument using the bite-wing localizing ring 1402, the bite-wing indicator arm 1406 and the interproximal bite-block 1404. The operator inserts the horizontal side of the film packet into one side of the bite-block. Then, flexing the film, the operator inserts the opposite side into the other side of the bite-block making sure that the all-white side of the film is facing the X-ray PID. In step 1400D, the operator centers the film. In step 1400C, with the bite-block lying on the occlusal surface of the mandibular teeth, the anterior edge of the film is aligned with the distal portion of the second bicuspid. It is preferred that the bite-block rests on the opposite side of the arch to the teeth being radial graphed as shown in 1410 of FIG. 14C. In step 1400D, the patient is instructed to bite down firmly and check to insure that the correct film position has been maintained in 1412 of FIG. 14C. The steps 1400E–H are similar to steps 1300E–H and a description thereof is referred to the corresponding sections of the specification. With the present invention, the exemplary X-ray negative 1414 is developed.

It will be appreciated from the foregoing that the present invention provides a rapid system, method and apparatus for assembling a positioner for performing a dental X-ray by providing color coded parts for easy assembly. Although the foregoing description is directed to use of the anterior, posterior and bite-wing exams, it will be appreciated that the present invention is not limited thereby but may be applicable to X-ray exams of any kind including medical X-rays. It will further be appreciated that the present invention provides a cost-effective solution to the problem of interchangeable positioner components while maintaining the interchangeability of the components thereof.

Although preferred embodiments of the present invention and modifications thereof have been described in detail herein, it is to be understood that this invention is not limited to those precise embodiments and modifications, and that other modifications and variations may be effected by one skilled in the art without departing from the spirit and scope of the invention as defined by the appended claims.

We claim:

1. A color coding system for color coding a dental positioner having components when combined according to said color coding form said dental positioner which guides an x-ray for x-raying a particular dental area, said system comprising:

a plurality of components constituting said dental positioner which when combined form said dental positioner which guides said x-ray for x-raying said particular dental area; and a color-coding for color coding a number of said components for identifying said components as corresponding to said particular dental area to be x-rayed such that, when said components are combined in accordance with said color-coding, said dental positioner formed guides said x-ray for x-raying said particular dental area.

2. The system according to claim 1, wherein said dental positioner when combined according to said color-coding guides said x-ray such that said x-ray is substantially perpendicular to said dental area x-rayed.

3. The system according to claim 1, wherein said dental positioner has at least one color-coded component for holding x-ray film in a mouth and at least one color-coded component for receiving an x-ray cone which transmits said x-ray.

4. The system according to claim 1, wherein said dental area is one of a plurality of types of dental areas; wherein said components are color-coded according to different types of dental areas.

5. The system according to claim 4, wherein the different types of dental areas are distinguished by different bites of a mouth.

6. The system according to claim 4, wherein the different types of dental areas are distinguished by different types of x-ray film to photograph associated different areas.

7. The system according to claim 3, wherein said color-coded component for receiving an x-ray cone is an aiming ring and said color-coded component for holding is a bite block.

8. The system according to claim 7, wherein said aiming ring and said bite block are both color coded to a particular dental area.

9. The system according to claim 7, wherein said components further include an indicator arm for coupling said aiming ring to said bite block.

10. The system according to claim 9, wherein said bite block is a bite-wing block.

11. The system according to claim 7, wherein said color-coding color codes said aiming ring to a bite block according to the anterior and posterior areas of the mouth.

12. A color coding method for color coding components of a dental positioner which when combined according to said color coding form said dental positioner which guides an x-ray for x-raying a particular dental area, said method comprising the steps of:

providing a plurality of components constituting said dental positioner which when combined form said dental positioner which guides said x-ray for x-raying said particular dental area; and color-coding a number of said components according to said dental area such that, when said components are combined in accordance with said color-coding, said dental positioner formed guides said x-ray for x-raying said dental area.

13. The method according to claim 12 wherein said step of providing provides said components such that when combined in accordance with said color coding form said dental positioner which guides said x-ray substantially perpendicular to said dental area.

14. The method according to claim 13, wherein said step of providing provides a color-coded component for holding x-ray film to image said x-raying and a color-coded component which receives an x-ray cone which transmits said x-ray.

15. The method according to claim 12, wherein said step of color-coding color codes said components according to one of a plurality of types of dental areas.

16. The method according to claim 15, wherein said step of color-coding color codes said components according to a type of dental area distinguished by a type of bite.

17. The method according to claim 15, wherein said step of color-coding color codes said components according to a type of dental area distinguished by type of area of a mouth.

18. The method according to claim 14, wherein said step of providing provides an aiming ring as said color-coded component for receiving said x-ray cone and a bite block as said color-coded component for holding said x-ray film.

19. The method according to claim 18, wherein said step of providing provides an indicator arm for coupling said aiming ring and said bite block.

20. The method according to claim 18, wherein said step of color coding color codes a particular aiming ring to a particular bite block according to anterior and posterior areas of the mouth.

21. The method according to claim 20, wherein the step of providing components provides as a bite block a bite-wing b lock.

22. A method for assembling a dental positioner by combining a number of color-coded components which when combined according to color coding form said dental positioner which guides an x-ray for x-raying a particular dental area, said method comprising the steps of:

determining particular ones of said number of said components which when combined according to said color coding form said dental positioner which guides said x-ray for x-raying said particular dental area; and assembling said particular ones of said components according to said color-coding to form said dental positioner which guides said x-ray for x-raying said particular dental area.

23. The method according to claim 22, wherein said step of assembling assembles a holding device for holding x-rays with a positioner for receiving an x-ray cone which transmits said x-ray.

24. The method according to claim 22, further comprising the step of inserting the assembled components in a mouth such that an axis of said x-ray is perpendicular to the particular dental area to be x-rayed.

25. The method according to claim 23, wherein said holding device is a bite block and said positioner is an aiming ring.

26. The method according to claim 25, wherein said color-coded components include an indicator arm.

* * * * *